United States Patent [19]
Kit et al.
[11] Patent Number: 4,703,011
[45] Date of Patent: Oct. 27, 1987

[54] THYMIDINE KINASE DELETION MUTANTS OF BOVINE HERPESVIRUS-1

[75] Inventors: Malon Kit; Saul Kit, both of Houston, Tex.

[73] Assignees: NovaGene, Inc.; Baylor College of Medicine, both of Houston, Tex.

[21] Appl. No.: 796,840

[22] Filed: Nov. 12, 1985

[51] Int. Cl.[4] ........................ C12N 7/04; C12N 15/00; A61K 39/12

[52] U.S. Cl. ................................ 435/236; 435/172.1; 424/89; 935/65

[58] Field of Search .................. 435/172.1, 172.3, 235, 435/236; 424/89; 935/65

[56] References Cited

U.S. PATENT DOCUMENTS

| | | | |
|---|---|---|---|
| 3,634,587 | 1/1972 | Ament et al. | 424/89 |
| 3,925,544 | 12/1975 | Shechmeister et al. | 424/89 |
| 4,291,019 | 9/1981 | Lupton et al. | 424/89 |
| 4,514,497 | 4/1985 | Kit et al. | 435/235 |
| 4,569,840 | 2/1986 | Kit | 435/238 X |

FOREIGN PATENT DOCUMENTS

| | | | |
|---|---|---|---|
| 141458 | 5/1985 | European Pat. Off. | 424/89 |

OTHER PUBLICATIONS

Kit et al., Virology, vol. 130, pp. 381-389 (1983).
Qavi et al., Abst. Annu. Meet. Am. Soc. Microbiol 83, "Isolation of Thymidine Kinase Negative Infections Bovine Rhinotracheitis Virus Mutants," 1983.
Mayfield et al., J. Virol., 47(1):259-264 (1983).
Post et al., Cell, 25:227-232 (1981).
Smiley, Nature, 385:333-335 (1980).
McDermott et al., J. Virol., 51(3):747-753 (1983).
Post et al., Cell. 24:555-565 (1981).
Pritchett et al., Am. J. Vet. Res., 45(12):2486-2489 (1984).

*Primary Examiner*—Esther M. Kepplinger
*Assistant Examiner*—Shawn P. Foley
*Attorney, Agent, or Firm*—Sughrue, Mion, Zinn, Macpeak and Seas

[57] ABSTRACT

Bovine herpesvirus type 1 (infectious bovine rhinotracheitis virus) mutants which fail to produce any functional thymidine kinase as a result of a deletion in the thymidine kinase gene. The deletion in the thymidine kinase gene attenuates the viruses so that they can be used as an active agent in a modified live-virus vaccine against infectious bovine rhinotracheitis. This invention also relates to methods for the production and use of the same.

25 Claims, 4 Drawing Figures

TRANSLATION OF LATK16

FIG. 4

2
TCGAGCGCGCCCGCGCGCCGCCCCCCTCCTCCGCGTCACGGCGGCGCGGCCCGCGCGCGCCGACTCCGCCGCCGGTCC

82
GCCTCCTCCGCCCGGCGCGCCGCCTCCTCCAGGTCCGCGAGCACGGCGGCTACCTCCGCCACCGGGCCTCAATGGGCCGG

162
ATGCGCGCGTCGACTTCCGCGCCCGCGGCGTCTGCCTTCGCCAGCAGGTTGTCCGCGGCCGCTGCCGGCCTGGTTCCGCG

242
CCCGCCGCCTCGCGGCCAGCTCCCGCGCGGGCGCGTCCGCGTCCCCAACTCCGCGCGAAGACGGGCTCGTCCCAGAAGCG

322
CAGCGGAAAGGCCGGCGTATAAAATTTCGCTCGTCCGGTACAAAGACGCGGTCCGCGACTGCGTGGATGTCCACGCCCAG

402
GCAAGCAAACTCTAAACGCCCGAGCGCCATGGCCCCGATGCCGCCACAAAGAGCGCCGAAATTTCGCCCAGGCACGCCGC

482
GCCGCCCGACGCGTCTTTAGCGCACCCGCCGGCGCTGTTGCCCGCGTGCCTGCTGGCCGCCCACCGGCGGCCGCTGTCCC

562
CGGCCTCAGCAGGGCCGGGGTCGCCGGCGGGCGGCCGCGGGGTGCGGCCACAGCCGCCCTTTTGCCCGTAGCCAGGGGAA

642
GCGGCTGCCCCTTCTGCCGCCGCGGCCGCGGTTGCTCGGCTTTGCGTTTGCCCCGCGGCGATCGCCCCGCTCGCCGCGAA

722
CGCGCGCGCGAATGGGGCGTACTCGGCGAGCCCGGCTATTATAGCCTCAAGGCGCGCCGCGTTGCTAGCGATCGTCTG

802
GGCCGGCAGGCGCGTCACTCTGAGCACGCGCATGCCCCGCTGGGAGACGAACACCTGCACCGGCGCTAGGACCACCGGGT

882
CTGGGCCCGGGGGGGCGAGATCGCGCACAAGCCGGGCCGAGTCGCGCAGCTGCCGCAGCCCCCCGAGGCGCTGGTCCATC

962
TTGCTGGGCGTGTTCATGTTCGTTGAAAAACGGCACGTCTTCAGCTCCACGATAAGACAGACGGCCCGGGCGTGCCCTGC

36 ▼

1042
CTCCGCGACCCGGAGTAGGCACACGCAATCGGGCCGCCGGCTTTGCAGGTTTACCTCAAAGCTCAGAGACACGCCCACGA

46 ▼

1122
CCTGCTTAAAAACCTCCGGGGCGCCAAACTTGCCCAAAAGCTGGGCGAGGCGCGGGCGCAGCTTCTGCGCGCCAACCGCC

1202
GCGCGTGCGTCGCAAGCCAGCGCCTCGTAAAAGCGGCTGTGGCACCGGATCCCGGCGCGCAGGCGCGCACGTCGGTCGCG

1282
GTCGCGCGCC MET ALA GLU PRO ALA ARG ALA LEU ARG VAL VAL ARG ILE TYR LEU ASP GLY
ATG GCC GAG CCC GCG CGC GCT CTC CGC GTC GTG CGT ATC TAC CTG GAC GGC

1343
ALA HIS GLY GLN GLY LYS THR THR THR GLY ARG ALA LEU ALA ALA ALA SER THR ALA GLY
GCG CAC GGG CAG GGA AAG ACA ACA ACG GGC CGC GCG CTC GCG GCC GCT TCC ACC GCT GGG

1403
GLU GLY VAL LEU PHE PHE PRO GLU PRO MET ALA TYR TRP ARG THR MET PHE GLY THR ASP
GAG GGC GTG CTC TTT TTC CCG GAG CCG ATG GCG TAC TGG CGC ACG ATG TTT GGT ACG GAC

1463
ALA LEU SER GLY ILE LEU ALA ALA SER ALA ARG CYS ALA ALA ALA SER HIS GLY SER ALA
GCC TTA AGT GGG ATC CTC GCG GCG TCT GCG CGA TGC GCC GCA GCC TCG CAC GGG AGC GCA

1523
ARG ALA ARG ARG ALA GLY ALA PRO ARG ARG ARG GLY ARG GLY GLY PRO GLY CYS VAL LEU
CGC GCG CGG CGG GCC GGC GCA CCG CGC AGA CGC GGA CGC GGC GGG CCT GGT TGC GTA CTA

1583
PRO GLY GLN VAL ARG GLY PRO VAL LEU ASN PHE ALA ARG ALA CYS PRO ARG CYS CYS ALA
CCA GGC CAG GTT CGC GGC CCC GTA CTT AAT TTT GCA CGC GCG TGT CCG CGC TGC TGC GCC

FIG. 4 CONT.

```
1643
ALA TRP ALA GLY ALA GLY ARG ARG ALA GLY GLY PRO SER CYS SER THR ALA THR PRO TRP
GCC TGG GCC GGC GCC GGG CGG CGA GCT GGT GGA CCC TCG TGT TCG ACC GCC ACC CCG TGG

1703
ARG ALA CYS LEU CYS TYR PRO PHE ALA ARG TYR CYS LEU ARG GLU ILE ASN ALA GLU ASP
CGC GCG TGC CTC TGC TAC CCC TTC GCC CGC TAC TGC CTC CGC GAG ATC AAC GCG GAA GAT
                                                                          BGL II
1763
LEU LEU MET LEU ALA ALA ALA MET PRO PRO GLU ALA PRO GLY ALA ASN LEU VAL VAL CYS
CTG CTC ATG CTC GCG GCC GCC ATG CCC CCG GAA GCG CCC GGG GCC AAC CTC GTC GTG TGC

1823
THR LEU PRO PRO ALA GLU GLN GLN ARG ARG LEU ALA ALA ARG ALA ARG PRO GLY ASP ARG
ACC CTC CCC CCG GCC GAG CAA CAG CGC CGC CTG GCG GCG CGG GCC AGG CCC GGA GAC CGC

1883
ALA ASP ALA GLY PHE LEU VAL ALA VAL ARG ASN ALA TYR ALA LEU LEU VAL ASN THR CYS
GCG GAC GCG GGC TTT CTG GTC GCT GTG CGC AAT GCT TAC GCG CTC CTG GTG AAC ACG TGC

1943
ALA PHE LEU ARG ALA GLY ALA HIS GLY ALA THR ALA GLY THR ARG TRP SER GLY ARG THR
GCT TTC CTG CGC GCG GGG GCG CAT GGC GCG ACG GCT GGG ACG CGC TGG AGT GGG CGG ACG

2003
GLN MET HIS TRP PRO ARG SER GLN THR PRO VAL VAL MET ASN ALA LYS CYS ALA GLY ALA
CAA ATG CAT TGG CCG CGC TCG CAG ACC CCA GTT GTG ATG AAT GCA AAA TGC GCC GGC GCC

2063
GLY LEU ARG ASP THR LEU PHE ALA ALA LEU LYS CYS ARG GLU LEU TYR PRO GLY GLY GLY
GGC CTG CGC GAC ACC CTG TTC GCG GCG CTC AAG TGC CGC GAG CTC TAC CCG GGC GGC GGG
                                                         SAC I
2123
THR GLY LEU PRO ALA VAL HIS ALA TRP ALA LEU ASP ALA LEU ALA GLY ARG LEU ALA ALA
ACG GGC TTG CCC GCG GTT CAC GCC TGG GCG CTG GAC GCC CTG GCC GGC CGC CTC GCC GCC

2183
LEU GLU VAL PHE VAL LEU ASP VAL SER ALA ALA PRO ASP ALA CYS ALA ALA ALA VAL LEU
CTC GAG GTG TTC GTG CTG GAC GTG TCC GCG GCG CCA GAC GCG TGC GCG GCC GCC GTA CTG

2243
ASP MET ARG PRO ALA MET GLN ALA ALA CYS ALA ASP GLY ALA ALA GLY ALA THR LEU ALA
GAC ATG CGG CCC GCC ATG CAG GCC GCT TGC GCG GAC GGG GCG GCG GGC GCG ACG CTG GCG

2303
THR LEU ALA ARG GLN PHE ALA LEU GLU MET ALA GLY GLU ALA THR ALA GLY PRO ARG GLY
ACC CTG GCG CGT CAG TTC GCG CTA GAG ATG GCG GGG GAG GCC ACG GCG GGC CCT AGG GGA

2363
LEU ***  AGCTGCCCCTGCGCTCGCTCGCTCGCTGCATTTGCGCCCCGATCGCCTTACGGGGACTCGGCGCTCGGCGG
CTA TAA

2440
ATCCCCTCCCGGCCCCGCCGCGAAGCAGGCCGCCAGACAAAAAAATGCGGCGCCCGCTCTGCGCGGCGCTATTGGCAGCG

2520
GCTGTCCTCGCGCTCGCCGCGGGCGCCCCCGCCGCCGCCCGCGGCGGGGGCGCCGAAGCCAGGGCAGCACAGAGACGCCC

2600
GATACGAAATCGAAGAGTGGGAAATGGTGGTCGGAGCCGGGCCGGCCGTGCACACGTTCACCATCCGCTGCCTCGGGCCG

2680
CGGGGCATTGAGCGCGTGGCCCACATTGCAAACCTCAGCCGGCTGCTGGACGGGTACATAGCGGTCCACGTTGACGTTGC

2760
GCGCACCTCTGGCCTGCGGGACGCCATGTTTTTCCTGCCGCGCGCGGCCGTCGAC

THE MOLECULAR WEIGHT OF THIS PROTEIN IS  36902.5
```

THYMIDINE KINASE DELETION MUTANTS OF BOVINE HERPESVIRUS-1

FIELD OF THE INVENTION

The present invention relates to bovine herpesvirus type 1 viruses which fail to produce any functional thymidine kinase as a result of a deletion in the thymidine kinase gene, vaccines against infectious bovine rhinotracheitis containing the same and methods for the production and use of the same.

BACKGROUND OF THE INVENTION

I. Infectious Bovine Rhinotracheitis

Bovine herpesvirus type 1 (hereinafter "BHV-1"), more commonly known as infectious bovine rhinotracheitis virus (hereinafter "IBRV"), has been associated with respiratory, reproductive, enteric, occular, central nervous system, neonatal, mammary, and dermal infections of cattle. Evidence for the association of IBRV with diseases of the respiratory tract was first obtained in the early 1950's. It has since become apparent that infectious bovine rhinotracheitis (hereinafter "IBR") has a worldwide distribution. Clinical symptoms are characterized by a sudden onset of hyperthermia, anorexia, and depression. The severe inflammation of the epithelial surfaces of the respiratory membranes often progresses to a necrotic rhinotracheitis (see: Schroeder, R. J. and Moys, M. D., *J. Am. Vet. Med. Assoc.* 125:471–472 (1954); McKercher, D. G., Moulton, J. E., and Jasper, D. E., *Proc. U.S. Livestock Sanit. Assoc* 58:260–269 (1955); Gibbs, E. P. J. and Rweyemamu, M. M., *The Vet. Bull.* 47:317–343 (1977); Kahrs, R. F., J. Am. *Vet Med.Assoc.* 171:1055–1066 (1977); Moorthy, A. R. S., ,Vet. Record 116:98 (1985); Ross, H. M., Vet. Record 113:217–218 (1983); Guy, J. S., PotgieteR, L. N. D., McCracken, M., and Martin, W., *Am. J. Vet. Res.* 45:783–785 (1984); and Engels, M., Steck, F., and Wyler, R., *Arch. Virol,* 67:169–174 (1981)).

In natural outbreaks of the respiratory form of the disease, conjunctivitis, manifested by a copious discharge, extensive hyperemia and edema of the conjunctiva, is also prominent. Infectious pustular vulvovaginitis and balanoposthitis are also caused by BHV-1, and are characterized by hyperemia of the vulvovaginal and preputial mucous membranes. This can lead to pustule formation and ulceration.

The spread of the disease in naturally and artificially bred cattle poses a serious problem, especially with the continued, widespread use of frozen semen. Recurrent shedding of virus from infected bulls also constitutes a significant threat to the artificial insemination industry in the United States and to the worldwide distribution of bovine germ plasm. The incrimination of BHV-1 as an etiologic agent of oophoritis and salpingitis with resultant infertility and sterility adds to the seriousness of the infection.

BHV-1 is widely recognized as a cause of abortion, stillbirths, and infertility. Most naturally occurring abortions occur between the fourth and seventh months of gestation, but cattle may abort from BHV-1 infections throughout gestation. Respiratory disease and conjunctivitis may or may not be observed prior to abortion.

Meningoencephalitis is another of the sequela to BHV-1 infection. Neurotropic symptoms are observed most often in calves under 6 months of age. The rate of encephalitis may vary from an occasional animal to a large portion of the herd.

BHV-1 infections of species other than cattle have been described (see: Fulton, R. W., Downing, M. M, and Hagstad, H. V., *Am. J. Vet. Res.* 43:1454–1457 (1982) and Lupton, H. W., Barnes, H. J., and Reed, D. E., *Cornell Vet.* 70:77–95 (1980)). Natural infections occur in swine, goats, water buffalo, wildebeests, ferrets, and mink. BHV-1 has been blamed for epizootics of vaginitis and balanitis in swine, and BHV-1 has been isolated from stillborn and newborn pigs in herds with a history of reproductive problems. According to serologic studies, about 11% of swine sera from Iowa and Texas herds contain BHV-1 antibody titers. Experimental infections have been established in swine fetuses, goats, mule deer, ferrets, and rabbits (see: Joo, H. S., Dee, S. A., Molitor, T. W., and Thacker, B. J., *Am. J. Vet. Med. Assoc.* 45:1924–1927 (1984)).

The severity of illness resulting from BHV-1 infections depends upon the virus strain and on the age of the animal affected. After recovery from infection, animals may show clinical signs of recurrent disease without being reexposed to the virus. Recurrent disease without reexposure occurs because the virus remains dormant, i.e. latent, in neurons of the sensory ganglia of its host and can be reactivated, even after long periods (see: Homan, E.J. and Easterday, B. C., *J. Infect. Dis.* 146:97 (1982); Homan, E. J. and Easterday, B. C., *Am. J. Vet. Res.* 44:309–313 (1983); and Ackermann, M., Peterhans, E., and Wyler, R., ,Am. J. Vet. Res. 43:36–40 (1982)). Dexamethasone treatment can also provoke nasal shedding of the virus with or without clinical symptoms of active IBR. This suggests that reactivation and release from neuronal sites and, possibly, persistent infection of other tissues can occur (see: Rossi, C. R., Kiesel, G. K., and Rumph, P. F., *Am. J. Vet. Res.* 43:1440–1442 (1982)).

II. Known IBR Vaccines

Currently, three types of IBR vaccines are being employed: (1) killed virus vaccines, (2) subunit vaccines, and (3) modified live-virus (hereinafter "MLV") vaccines (see: U.S. Pat. Nos. 3,925,544; 4,291,019; and 3,634,587). Killed IBR vaccines are produced by treating the virus with chemicals, such as formalin or ethanol and/or physical agents, such as heat or ultraviolet irradiation. Subunit IBR vaccines are prepared by solubilizing BHV-1-infected cell cultures with nonionic detergents. Early MLV vaccines were designed for parenteral administration and consisted of virus attenuated by rapid passage in bovine cell cultures. More recently, parenterally administered MLV vaccines have been attenuated by adaption of BHV-1 to porcine or canine cell cultures, by adaption to growth in cell culture at a low temperature (30° C.), or by selection of heat-stable virus particles (56° C. for 40 minutes). Specialized types of MLV vaccines are those administered intranasally. These MLV vaccines are attenuated by serial passage in rabbit cell cultures or by treatment of BHV-1 with nitrous acid followed by selection fo temperature-sensitive mutants. A temperature-sensitive virus is one that replicates efficiently at about 32° C.–38° C., but not at about 39° C. –41° C. (see: Todd, J. D., Volenec, F. J., and Paton, I. M., *J. Am. Vet. Med. Assoc.* 159:1370–1374 (1971); Kahrs, R. F., Hillman, R. B., and Todd, J. D., *J. Am. Vet. Vet. Med. Assoc.* 163:437–441 (1973); Smith, M. W., Miller, R. B., Svoboda, I., and Lawson, K. F., *Can. Vet. J.* 19:63–71

(1978); Zygraich, N., Lobmann, M., Vascoboinic, E., Berge, E., and Huygelen, C., *Res. Vet. Sci.* 16:328–335 (1974); and U.S. Pat. Nos. 3,907,986 and 4,132,775).

All of the currently available IBR vaccines have serious disadvantages and have, therefore, proved unsatisfactory in commercial use. More specifically, although killed IBR vaccines are considered by some to be safer than MLV vaccines, i.e., they cannot establish latency and they eliminate the problem of postvaccination shedding, they are expensive to produce, must be administered several times, and disadvantageously require adjuvants. In addition, with their use, there is the possibility of fatal hypersensitivity reactions and nonfatal urticaria. Further, some infectious virus particles may survive the killing process and thus cause disease. Moreover, cattle vaccinated with killed IBR vaccines can be infected at a later time with virulent virus and can shed virulent virus, thereby spreading infection in the herd (see: Frerichs, G. N., Woods, S. B., Lucas, M. H., Sands, J. J., *Vet. Record* 111:116–122 (1982)). In one study, a killed IBR vaccine using a 5-component adjuvant was found entirely ineffective in producing immunity, preventing disease, and suppressing propagation and reexcretion of virulent virus (see: Msolla, P. M., Wiseman, A., Selman, I. E., Pirie, H. M., and Allen, E. M., *Vet. Record* 104:535–536 (1979)). That is, following challenge exposure to virulent virus, vaccinated animals exhibited clinical signs and virus excretion responses virtually identical to unvaccinated animals. Further, in marked contrast to calves which recovered from natural infection, these calves transmitted virulent virus to in-contact controls. Thus, although killed IBR vaccines can provide some protection against IBR, they are generally inferior to MLV vaccines in providing long-term protection.

Subunit vaccines are often less toxic than killed virus vaccines, and may induce novel immunologic effects which can be of significant value. The technique for subunit vaccine preparation involves removal of capsid proteins, while leaving intact antigens that elicit protective immunity. This creates a potential for the development of serologic procedures to differentiate vaccinated from naturally infected animals. Further, subunit vaccines may be antigenic, yet contain no live virus and, thus, cannot be transmitted to other animals, cause abortion, or establish latency. In one study, a single dose of subunit vaccine markedly modified challenge infection, and two doses prevented clinical disease and virus shedding in all vaccinated animals after challenge exposure with 106 PFU of the standard virulent BHV-1(Cooper) strain inoculum. However, the possibility that a latent infection was established could not be excluded (see: Lupton, H. W. and Reed, D. E., *Am. J. Vet. Res.* 41:383–390 (1980)). When testing another IBR subunit vaccine previously found to elicit a strong immune response in adult cattle, the vaccine failed to do so in younger animals and it did not protect the animals against respiratory disease (see: le Q. Darcel, C. and Jericho, K., *Can. J. Comp. Med.* 45:87–91 (1981)). Other disadvantages of subunit vaccines are the high cost of purification and the requirement of several injections with adjuvant.

MLV IBR vaccines have the important advantage that they produce rapid protection and activate cell-mediated and humoral components of the immune system. In the case of intranasal vaccination, localized immune responses that suppress later replication of virulent BHV-1 in the respiratory tract contribute significantly to protection. The local immune responses include production of interferon and antibodies in nasal secretions (see: Kucera, C. J., White, R. G., and Beckenhauer, W. H., *Am. J. Vet. Res.* 39:607–610 (1978)).

Extensive utilization of MLV IBR vaccines has reduced the frequency of occurrence of IBR. However, none of the available MLV IBR vaccines are entirely satisfactory. More specifically, there is concern as to their safety, especially if the vaccine virus itself produces latency and may be shed and transmitted to susceptible cattle. Vaccination with available MLV preparations is also ineffective in preventing latent infections following exposure to virulent BHV-1. For example, in one study, a MLV IBR vaccine, obtained by passing BHV-1 43 times in porcine testes cells followed by 8 passages in monolayer cultures of bovine testes at 30° C., was used to vaccinate calves (see: Narita, M., Inui, S., Nanba, K., and Shimizu, Y., *Am. J. Vet. Res.* 41:1995–1999 (1980)). At 49 days after the calves were challenge-exposed to virulent BHV-1, the calves were treated with dexamethasone and latent virus infection was demonstrated through signs of recurrent infection.

Maximal utilization of intramuscularly (hereinafter "IM") administered MLV IBR vaccines has been especially hampered by the hazards of vaccine-induced abortions. That is, abortion rates as high as 60% have been reported after IM injection of some MLV IBR vaccines (see: Kahrs, R. F., *J. Am. Vet. Med. Assoc.* 171:1055–1064 (1977) and Kendrick, J. W. and Straub, OC., *Am. J. Vet. Res.* 28:1269–1282 (1967)). In addition, with the MLV IBR vaccines currently in use, there is the danger of reversion to virulence.

In a search for safer MLV IBR vaccines, specialized vaccines have been developed (see: Todd, J. D., Volenec, F. J., and Paton, I. M, *J. Am. Vet. Med. Assoc.* 159:1370–1374 (1971); Kahrs, R. F., Hillman, R. B., and Todd, J. D., *J. Am. Vet. Med. Assoc.* 163: 427–441 (1973); Smith, M. W., Miller, R. B., Svoboda, I., and Lawson, K. F., *Can. Vet. J.* 19:63–71 (1978); Zygraich, N., Lobmann, M., Vascoboinic, E., Berge, E., and Huygelen, C., *Res. Vet. Sci.* 16:328–335 (1974); and Kucera, C. J., White, R. G., and Beckenhauer, W. H., *Am. J. Vet. Res.* 39:607–610 (1978)). These vaccines have been found to be immunogenic and safe for intranasal (hereinafter "IN") inoculation to pregnant cattle and can prevent abortions in pregnant cows which have been challenge-exposed to virulent BHV-1. However, they have a disadvantage in that they can only be administered by the IN route. This is because, when administered IN, one such IBR vaccine replicates to a limited extent at the lower temperature of the upper respiratory tract. However, when administered IM, the vaccine replicates poorly or not at all at normal body temperature (see: Zygraich, N., Lobmann, M., Vascoboinic, E., Berge, E., and Huygelen, C., *Res. Vet. Sci.* 16 328–335 (1974)). On the other hand, another IBR vaccine is insufficiently attenuated for IM administration to pregnant animals although safe when given IN (see: Todd, J. D., *J. Am. Vet. Med. Assoc.* 163: 437–441 (1973). Furthermore, some of the vaccine strains produce mild or moderate respiratory disease even after IN administration, and they do not prevent signs of IBR following field challenge exposure (see: Kahrs, R. F., Hillman, R. B., and Todd, J. D., *J. Am. Vet. Med. Assoc.* 163:437–441 (1973)).

Accordingly, neither the IM-administered MLV IBR vaccines, which are unsafe for pregnant cows, nor the MLV IBR vaccines that must be administered IN fits comfortably into many of the current management practices. That is, vaccination of large numbers of cattle by the IN route is inconvenient and potentially dangerous to animal handlers. Additionally, screening to identify pregnant animals prior to immunization is often not desirable or cost effective. The development of a vaccine which can be safely administered either IN or IM in stressed feedlot cattle, in breeding bulls, and even in pregnant cows would facilitate disease prevention, be more cost effective, and be compatible with current management regimens. The present invention was developed in order to meet these needs.

III. Attenuated Properties of Thymidine Kinase-Negative Herpesvirus Mutants

Recently, a temperature-resistant, thymidine kinase-negative (hereinafter "tk−") IBR vaccine has been developed which overcomes many of the problems that have limited the use of currently available vaccines (see: Kit, S. and Qavi, H., *Virol.* 130:381–389, (1983) and U.S. patent application Ser. No. 516,179, filed July 21, 1983). This BHV-1 mutant replicates equally well in rabbit skin and in bovine tracheal or bovine turbinate cells at either 39.1° C. or 34.5° C. In contrast, temperature-sensitive BHV-1 strains replicate only $10^{-4}$ to $10^{-7}$ as well at 39.1° C. as at 34.5° C. In addition, this mutant lacks the ability to produce functional thymidine kinase (hereinafter "TK") enzyme activity in infected cells as a result of a mutagen-induced mutation. These two characteristics, i.e. temperature resistance and tk−, directly contribute to the superiority of this virus as a vaccine as discussed in more detail below.

Temperature-sensitive viruses are a specialized type of attenuated virus and contain mutations in genes essential for virus replication. That is, they are "crippled" viruses and replicate poorly, if at all, at normal body temperatures. Therefore, IN-administered vaccine viruses with temperature-sensitive mutations must be restricted to the nasal mucosa and the surface epithelial cells of the upper respiratory tract, which has a lower temperature. Further, IN-administered vaccine viruses regularly shed more virus in nasal secretions than IM-administered vaccine viruses, and they produce latency as readily as do regular non-temperature-sensitive viruses. On the other hand, temperature-resistant viruses replicate efficiently at 39.1° C. and are not attenuated through "crippling" mutations in genes required for virus replication. Further, they provide stronger immune responses than temperature-sensitive viruses because the resistance to higher temperatures allows them to replicate efficiently in tissues deep within the body and in febrile animals. Moreover, the option exists of administering these viruses by IM, IN, or other routes.

Herpesvirus-encoded TK enzymes are distinct from host cell TK enzymes in immunological and biochemical properties. Herpesvirus TK enzymes facilitate herpes-virus replication in nondividing cells. Because many herpesviruses are neurotropic viruses normally capable of both productive and latent infection in nondividing neural cells, it has been hypothesized that tk− virus mutants may be less neurovirulent than wild-type thymidine kinase-positive (hereinafter "tk+") strains.

Many recent experiments utilizing animal model systems demonstrate that herpes simplex type 1 (hereinafter "HSV-1") tk genes are important for virulence (see: Klein, R. J., *Arch. Virol.* 72:143–160 (1982)). These studies have shown that tk− mutants of HSV-1 have reduced pathogenicity in mice, rabbits, and guinea pigs for herpes encephalitis, herpes keratitis, and herpes labialis. In addition, the tk− HSV-1 mutants: (i) are less likely to be reactivated from latency; (ii) protect laboratory animals against fatal infection from virulent tk+ viruses; and (iii) reduce the probability of colonization of sensory ganglia by superinfecting virulent tk+ viruses.

tk− mutants of HSV-2, *Herpesvirus tamarinus*, and pseudorabies virus are also less virulent than parental tk+ strains. Furthermore, restoration of the tk+ function by recombining tk− pseudorabies virus mutants with DNA fragments encoding the tk gene increases the virulence for mice, whereas converting the latter recombinat tk+ viruses once more to tk− mutants again diminishes virulence for mice (see: Kit, S., Qavi, H., Dubbs, D. R., and Otsuka, H., *J. Med Virol.* 12:25–36 (1983) and Kit, S., Kit, M., and Pirtle, E. C., *Am. J. Res.* 46:1359–1367 (1985)).

In guinea pigs, tk+ strains of HSV-2 replicate to high titers in the vagina and in the spinal cord. The guinea pigs infected intravaginally with tk+ viruses exhibit severe vesiculoulcerative genital lesions, urinary retention, hind-limb paralysis, and death in about 25% to 33% of the animals. The onset, magnitude, and duration of vaginal virus replication is about the same following tk− HSV-2 inoculation as that observed after tk+ HSV-2 inoculation. However, guinea pigs inoculated with tk− HSV-2 exhibit no deaths, little or no clinical illness, and only low titers of virus are detected in spinal cord homogenate cultures (see: Stanberry, L. R., Kit, S., and Myers, M. G., *J. Virol.* 55:322–328 (1985)). In addition, vaccination of guinea pigs with tk− HSV-2 modifies a subsequent tk+ HSV2 genital infection. That is, reinfection with tk+ HSV-2 is clinically inapparent, vaginal replication of tk+ HSV-2 is reduced, and ganglionic infection is prevented.

In addition to the preceding model experiments with laboratory animals, the attenuated properties of a tk− deletion mutant of pseudorabies virus for natural hosts has been demonstrated (see: U.S. Pat. No. 4,514,497 and Kit, S., Kit, M. and Pirtle, E. C., *Am. J. Vet. Res.* 46:1359–1367 (1985)).

Pilot experiments performed in 5- to 6-week-old pigs provided the initial evidence for the safety and efficacy of a pseudorabies virus tk− deletion mutant. These experiments demonstrated that pigs vaccinated IM or IN with $7.5\times10^{8}$ PFU of the pseudorabies virus tk− deletion mutant and then challenge-exposed IN with the very high dose of $6\times10^{8}$ PFU of the highly virulent Indiana-Funkhauser (Ind-F) strain of pseudo-rabies virus, had no clinical signs of illness after vaccination or after challenge exposure. Nonvaccinated pigs either died or became moribund before eventually recovering. In another study on a quarantined swine herd in Texas, more than 700 grower-finisher pigs, 224 nursery pigs, 128 females in all stages of pregnancy, 56 nonpregnant females, 7 boars, and 224 piglets were immunized with no adverse reactions (see: Kit, S., Kit, M., Lawhorn, B., and McConnell, S., *ASM Publication on Proceedings of the* 1984, *High Technology Route to Virus Vaccines,* American Society for Microbiology, Washington, D.C., pp. 82–99 (1985)). Finally, highly susceptible calves and weanling lambs were vaccinated with over 108 PFU of the pseudorabies virus tk− deletion mutant, but no disease signs were observed.

Two pilot studies in the natural host to assess the safety and efficacy of a temperature-resistant tk− mutagen-induced mutant BHV-1 vaccine virus, i.e., BHV- 1(B8-D53) (ATCC No. VR-2066) have also been completed (see: Kit, S., Qavi, H., Gaines, J. D., Billingsley, P., and McConnell, S., *Arch. Virol.* 86:63–84 (1985)).

In the first study, four groups of calves consisting of 19 Holstein steers and 1 freemartin, 3 months of age were used. Group 1 consisted of 7 calves vaccinated either IN or intravenously with $2\times10^7$ PFU of BHV-1(B8-D53) and challenged IN 56 days later with either $1.3\times10^8$ PFU BH V-1(Copper), i.e, the U.S. Dept. of Agriculture standard challenge BHV01, or with $2\times10^7$ PFU of BHV-1 (Los Angeles), i.e., the parental strain from which BHV-1B8-D53) was derived. Group 2 consisted of 3 calves vaccinated as above but not challenge-exposed with virulent BHV-1. Group 3 consisted of 4 calves that were not vaccinated, but were challenge-exposed IN with either the Cooper or Los Angeles strain of BHV-1. Group 4 consisted of 6 control calves that were neither vaccinated nor challenge-exposed. At 91 days after vaccination, calves from all four groups were stressed for 5 days with an intravenous injection of dexamethasone. On day 121 after vaccination, the dexamethasone treatment was repeated.

Vaccinated calves developed neutralizing antibodies but did not show clinical signs of IBR disease following IN challenge exposure to the virulent BHV-1 strains. BHV-1(B8-D53) vaccination reduced the multiplication of virulent BHV-1 in the nasal mucosa, but did not completely prevent development of a persistent infection by the challenge virus.

In the second study, 15 pregnant cows, seronegative for BHV-1, were used.

The cows were randomly assigned into one of two groups: (a) 5 cows to be vaccinated IM plus 2 contact controls; and (b) 3 cows to be vaccinated IM, 3 cows to be vaccinated intravaginally, and 2 contact controls. On day 1, 3.0×107 PFU of BHV-1(B8-D53) vaccine virus was given either by IM inoculation or by intravaginal instillation.

On day 45, the cows were segregated and randomized again for the virulent BHV-1(Cooper) challenge exposure segment of the study. The two groups consisted of (a) 5 IM- and 1 intravaginally vaccinated cows plus 1 nonvaccinated, nonchallenge-exposed contact control cow, and (b) 3 IM- and 2 intravaginally vaccinated cows, 2 nonvaccinated, challenge-exposed control cows, and 1 nonvaccinated, nonchallenge-exposed contact control cow.

The group (b) cows (excluding the contact control) were challenge-exposed IN on day 46, with 2.8×109 PFU of virulent BHV-1(Cooper).

All of the pregnant cows remained clinically normal throughout the 12-day observation period after BHV-1(B8-D53) vaccination.

After IN challenge exposure to virulent BHV-1(Cooper), replication IN of the challenge virus was detected, but the vaccinated cows did not develop any fever or clinical signs of disease. The non-vaccinated challenge control cows did show fever for 2–5 days and signs of respiratory distress, labored breathing, mucopurulent nasal discharge, and reduced food intake.

Live calves were born to all 15 of the pregnant cows used in this study. Precolostrum serum samples were obtained from calves born to 5 cows. All of these precolostrum samples were negative for BHV-1 virus-neutralizing antibodies, showing that neither the IM- or the intravaginally administered vaccine virus, nor the IN-inoculated challenge virus had infected the fetuses. Postcolostrum samples from calves born to seropositive cows were positive for virus-neutralizing antibodies.

In conclusion, the lack of clinical disease in the pregnant cows vaccinated with BHV-1(B8-D53) and challenge-exposed to BHV-1(Cooper) and the absence of BHV-1 antibodies in the precolostrum sera of newborn calves demonstrated the avirulence of this vaccine virus.

IV. Thymidine Kinase-Negative Herpesvirus Mutants

Several different types of herpesvirus mutants deficient in TK-inducing activity are known. Many of these mutants induce the synthesis of normal sized TK polypeptides, but without any functional TK activity. These mutants either have changed amino acids at the active centers of the enzyme or mutations that alter polypeptide folding. Other mutants, i.e., HSV-1(B2006), fail to induce the production of any TK polypeptide, possibly as a result of nonsense mutations at codons near the amino terminus of the polypeptide. Still other mutants induce inactive, truncated (or shortened) polypeptides because of translation-terminating (nonsense) codons in the middle of the tk gene. This type of mutation can be "suppressed" with "suppressor tRNAs" so that partial TK activity is restored. Yet other types of mutants induce TK enzymes with altered nucleoside substrate specificities. For example, wild-type (i.e., non-mutant) HSV-1 viruses induce TK enzymes that efficiently catalyze the phosphorylation of thymidine, deoxycytidine, and the nucleoside analogs, bromovinyldeoxyuridine, and acyclovir. However, HSV-1 mutants with altered substrate specificities induce TK activities with reduced, but significant, thymidine phosphorylating activity, yet no detectable acyclovir phosphorylating activity (or deoxycytidine or bromovinyldeoxyuridine phosphorylating activities). These mutants have changed amino acids at the nucleoside binding sites of the enzymes. Hence, affinities for nucleoside substrates are reduced in comparison with that of wild-type HSV-1-encoded TKs. Finally, $tk^-$ mutants with nucleotide deletions within the coding region of the tk gene fail to induce production of any functional TK polypeptide.

$tk^-$ herpesviruses with deletions in the tk gene are superior to spontaneous or mutagen-induced tk- mutants (see: U.S. patent application Ser. No. 516,179, filed July 21, 1983, and U.S . Pat. No. 4,514,497) containing only nucleotide changes in the tk gene for the following three reasons.

First, the herpesvirus deletion mutants have absolutely no TK-inducing activity because: (i) the deletion of amino acid coding sequences changes the tertiary structure and/or substrate binding sites of the TK enzyme in such a way that catalytic function is irrevocably lost; and (ii) those nucleotide deletions that are not divisible by 3 change the translational reading frame of the virus gene in coding the TK polypeptide. In contrast, mutants containing nucleotide changes only frequently exhibit partial TK-inducing activity. This is inappropriate for a vaccine because mutants with partial TK activity are often virulent (see: Gordon, Y., Gilden, D. H., Shtram, Y., Asher, Y., Tabor, E., Wellish, M., Devlin, M., Snipper, D., Hadar, J., and Becker, Y., *Arch. Virol.* 76:39–49 (1982); Klein, R. J., *Arch. Virol.* 72:143–168 (1982); and Tenser, R. B., Ressel S., and Dunstan, M. E., *Virol.* 112:328–334 (1981)).

Second, $tk^-$ herpesviruses with deletions in the tk gene cannot revert to $tk^+$.In contrast, $tk^-$ mutants containing only nucleotide changes in the tk gene can revert to tk+. tk+ revertants have restored virulence (see: Kit, S., Kit, M., and Pirtle, E. C., *Am. J. Vet. Res.* 46:1359–1367 (1985)), and working pools of tk− mutants can contain spontaneous tk+ revertants at a frequency of $10^{-3}$ to $10^{-5}$. These tk+ revertants can then have a selective advantage for in vivo replication over the tk− mutants. Most drug-induced tk− herpes-virus mutants have the potential to revert, even though the reversion frequency may be lower than the spontaneous reversion frequency, i.e., on the order about $10^{-5}$ to $10^{-7}$ (see: campione-Piccardo, J., Rawls, W. E., and Bacchetti, S., *J. Virol.* 31:286–287 (1979)).

Third, tk− herpesviruses with deletions in the tk gene can be distinguished from virulent field strains and from other vaccine strains by their tk− phenotypes, by their restriction endonuclease patterns, and by their Southern blotting molecular hybridization patterns (see: Kit, S., Kit, M., and Pirtle, E. C., *Am. J. Vet. Res.* 46:1359–1367 (1985)). These distinctions have practical importance. For example, if a vaccinated animal develops disease, it is important to know whether the vaccine virus caused the disease or whether infection by a virulent field strain did so.

General approaches for obtaining herpesviruses with deletions in the coding region of the tk gene are known. These methods have been used to obtain tk− deletion mutants of HSV-1, HSV-2, ,*Herpesvirus-tamarinus,* and pseudorabies virus (see: Smiley, J. R., *Nature* 385:333–335 (1980); Post, L. E., Mackem, S., Roizman, B., *Cell* 24:555–565 (1981); Post, L. E. and Roizman, B., *Cell* 25:227-232 (1981); McDermott, M. R., Smiley, J. R., Leslie, P., Brais, J., Rudzroga, H. E., and Bienenstock, J., *J. Virol.* 51:747–753 (1983), Kit, S., Qavi, H., Dubbs, D. R., and Otsuka, H., *J. Med. Virol.* 12:25–36 (1983); U.S. Pat. No. 4,514,497 and Kit, S., Kit, M., and Pirtle, E. C., *Am. J. Vet. Res.* 46:1359–1367 (1985)).

However, these approaches are not directly useful in the preparation of IBRV tk− deletion mutants since there is no teaching or suggestion therein of: (i) the identity of the IBRV DNA fragment that encodes the tk gene or for that matter its location on the IBRV genome; (ii) the approximate boundaries of the IBRV tk gene; or (iii) its nucleotide sequence. Heretofore, it has only been known that: (i) IBRV possesses a double-stranded, linear DNA genome of about 86 mega-daltons (137 kilobase pairs (hereinafter "kb" or "Kbp"), and an overall molar guanine plus cytosine content of about 70%; (ii) the IBRV genome is composed of L and S components which can exist in two isomeric forms; and (iii) the DNA genome of the Cooper strain of IBRV is cleaved by HindIII, BamHI, EcoRI, and HpaI restriction endonucleases to 15, 11, 7, and 7 fragments, respectively. The sizes of these fragments and their arrangement on the physioal map of IBRV DNA have also been described (see: Mayfield, J. E., Good, P. J., Van Oor, H. J., Campbell, A. R., and Reed, D. E., *J. Virol.* 47:259–264 (1983)).

To identify DNA fragments encoding herpesvirus tk genes, one or more of the following methods have previously been used: (i) molecular hybridization experiments, that is, experiments in which labeled DNA fragments from a known viral tk gene and DNA fragments from the unknown virus are hybridized to detect homologous nucleotide sequences; (ii) biochemical transformation of mutant tk− cells (e.g., mouse fibros blast LM(TK-)) to the tk+ phenotype; (iii) transfection or microinjection of hybrid plasmids containing the putative tk gene into LM(TK−) cells or mouse or frog eggs and then assaying for transient expression of TK enzyme activity; and (iv) marker transfer experiments with infectious DNA from a tk− mutant virus and hybrid plasmids containing the tk gene (see: Scangos, G. and Ruddle, F. H., *Gene* 14:1-10 (1981); Brinster, R. L., Chen, H. Y., Warren, R., Sarthy, A., and Palmiter, R. D., *Nature* 296:39–42 (1982); Otsuka, H., Hazen, M., Kit, M., Qavi, H., and Kit, S., *Virol.* 113:196–213 (1981); Kit, S., Qavi, H., Hazen, M., Trkula, D., and Otsuka, H., *Virol.* 113:452–464 (1981); Weir, J. P., Bajszar, G., and Moss, B., *Proc. Nat. Acad. Sci. USA* 79:1210–1214 (1982); Dubbs, D. R., Otsuka, H., Qavi, H., and Kit, S., *Virol.* 126:408–411 (1983); Otsuka, H., Qavi, H., and Kit, S., *Antiviral Res.* 2 301–311 (1982); McKnight, S. L. and , *Nucl. Acids Res.* 8:5931–5948 (1980); and Capecchi, M. R., *Cell* 22:479–488 (1980)).

However, in general, these methods are not applicable to the identification of the DNA fragment which encodes the IBRV tk gene. More specifically, high specific activity, 32P-labeled probes made by nick-translating. cloned HSV, pseudorabies virus, and *Herpesvirus tamarinus* tk genes do not hybridize to IBRV DNA fragments. Thus, the technique of molecular hybridization is not applicable to IBRV. That is, there is substantially no homology between the tk genes of the various herpesvirus species, i.e. the nucleotide sequences of the tk genes and the amino acid sequences of the TK enzymes of the various herpesvirus species are dissimilar. In addition, biochemical transformation experiments in which cloned IBRV DNA fragments are transfected into tk mutant mouse (LM(TK−)) or rabbit (RAB(BU)) cells do not yield colonies of tk+ cells containing integrated IBRV DNA sequences (see: Kit, S., Qavi, H., Hazen, M., Trkula, D., and Otsuka H., *Virol.* 113:452–464 (1981); Otsuka, H., Hazen, M., Kit, M., Qavi, H., and Kit, S., *Virol.* 113:196–213 (1981); Kit, S., Kit, M., Qavi, H., Trkula, D., and Otsuka, H., *Biochim. Biophys. Acta* 741:158–170 (1983)). Likewise( transfection of hybrid plasmids containing IBRV DNA fragments into RAB(BU) cells does not lead to the transient expression of TK activity, although TK activity is expressed in a control experiment in which the transfection of a hybrid plasmid containing the HSV-1 tk gene is used (see: Otsuka, H., Qavi, H., and Kit, S., *Antiviral Res.* 2:301-311 (1982)).

On the other hand, it has been found in the present invention that the DNA fragment encoding the IBRV tk gene can be identified through marker transfer experiments. It is to be emphasized that it has been found in the present invention that marker transfer experiments for the identification of the IBRV tk gene can only be performed if a tk− IBRV mutant, with a low reversion frequency to tk+, and a tk− mutant host cell permissive for IBRV are employed. As discussed in more detail below, it has been found in the present invention that the IBRV mutant (IBRV(B8-D53)) described in U.S. patent application Ser. No. 516,179, filed July 21, 1983, and the RAB(BU) cell line, described in Kit, S. and Qavi, H., *Virol.* 130:381-389 (1983), fill these needs. That is, IBRV(B8-D53) is an excellent starting material since it does not revert to tk+ even when the virus is propagated in tissue culture in a medium that selects for revertants or after two in vivo serial passages in calves. Similarly, RAB(BU) cells are excellent host cells for IBRV replication and they revert to tk+ with a very low frequency, i.e., less than $1\times10^{7}$.

Marker transfer experiments, and the in vitro transcription/translation studies described in the present invention, also permit the delineation of the approximate boundaries of the IBRV tk gene. Thus, for the first time, in the present invention, the IBRV DNA subfragment containing the tk gene to be sequenced and, also, the appropriate nucleotide sequence that could be deleted so as to disrupt the coding sequence of the IBRV tk gene has been identified.

SUMMARY OF THE INVENTION

An object of the present invention is to provide an IBR vaccine effective in controlling the spread of IBR disease in its various manifestations.

Another object of the present invention is to provide an IBR vaccine, wherein the vaccine can be safely and efficaciously administered intramuscularly, intranasally, or intravaginally.

Still another object of the present invention is to provide an IBR vaccine, wherein the vaccine can be administered safely to calves and to pregnant cows in all stages of pregnancy.

A further object of the present invention is to provide an IBR vaccine, wherein the vaccine virus fails to produce any functional TK enzyme activity as a result of either (i) a deletion in the coding sequence of the tk gene, alone or in combination with (ii) an insertion of an oligonucleotide linker sequence in place of the deletion.

A still further object of the present invention is to provide an IBRV vaccine, wherein the vaccine virus can replicate efficiently at temperatures ranging from about 30° C to 40° C, i.e. inclusive of temperature-resistant mutants.

Another object of the present invention is to provide an IBR vaccine, wherein the vaccine virus cannot revert to tk+ and is easily isolated from tk+ IBRV.

Still another object of the present invention is to provide an IBR vaccine, wherein the vaccine virus is distinguishable from any field strain virus and from any other BHV-1 vaccine virus.

A further object of the present invention is to provide an IBR vaccine, wherein the animal vaccinated with such does not acquire a dormant infection with pathogenic field strains.

A still further object of the present invention is to provide a method for the production and use of an IBR vaccine, wherein the vaccine virus cannot revert to tk+.

In an embodiment of the present invention, these above-described objects have been met by a highly attenuated IBRV which fails to produce any functional TK as a result of a deletion in the tk gene, and a MLV vaccine for IBR comprising (1) a pharmaceutically effective amount of said virus, and [2) a pharmaceutically acceptable carrier or diluent.

In another embodiment of the present invention, the above-described objects have been met by a process for producing a highly attenuated IBRV which fails to produce any functional TK as a result of a deletion in the tk gene comprising:

(1) Constructing a hybrid plasmid comprising a cloning vector and a DNA fragment of IBRV containing substantially all of the IBRV tk gene;

(2) Co-transfecting, in tk+ host cells, the hybrid plasmid of step (1) with infectious DNA from a tk− IBRV mutagen-induced mutant;

Selecting, in tk− host cells, for tk+ IBRV from the virus produced in step (2);

(4) Deleting DNA sequences from the hybrid plasmid of step (1) such that less than substantially all of the IBRV tk gene is present;

(5) Co-transfecting, in tk+ host cells, IBRV tk+ DNA derived from the tk+ IBRV obtained in step (3) with the resulting tk− hybrid plasmid of step (4); and (6) Selecting, in tk− host cells, for tk− IBRV from the virus produced in step (5) so as to produce tk− IBRV mutants which fail to produce any functional TK as a result of a deletion in the tk gene.

In still another embodiment of the present invention, an oligonucleotide linker is inserted in place of the deleted IBRV DNA in step (4) while retaining IBRV DNA sequences adjacent to each side of the deleted IBRV DNA fragments.

In a further embodiment of the present invention, the tk− IBRV-mutagen-induced mutant in step (2) is a temperature-resistant mutant such that the resulting mutant in step (6) is both temperature resistant and a tk− deletion mutant.

In an additional embodiment of the present invention, the above-described objects have been met by a process for producing a highly attenuated IBRV which fails to produce any functional TK as a result of a deletion in the tk gene comprising:

(1) Constructing a hybrid plasmid comprising a cloning vector and a DNA fragment of IBRV containing substantially all of the IBRV tk gene;

(2) Co-transfecting, in tk+ host cells, the hybrid plasmid of step (1) with infectious DNA from a tk− IBRV mutagen-induced mutant;

(3) Selecting, in tk− host cells, for tk+ IBRV from the virus produced in step (2);

(4) Deleting DNA sequences from the hybrid plasmid of step (1) such that less than substantially all of the IBRV tk gene is present;

(5) Co-transfecting, in tk+ host cells, IBRV tk+ DNA derived from the tk+ IBRV obtained in step (3) with the resulting tk− hybrid plasmid of step (4);

(6) Selecting, in tk− host cells, for tk− IBRV from the virus produced in step (5) so as to produce tk− IBRV mutants which fail to produce any functional TK as a result of a deletion in the tk gene; and (7) Propagating the resulting IBRV which fails to produce any functional TK as a result of a deletion in the tk gene of step (6) at a non-permissive temperature for a temperature-sensitive virus so as to select for and produce a temperature-resistant IBRV which fails to produce any functional TK as a result of a deletion in the tk gene.

BRIEF DESCRIPTION OF THE DRAWINGS

FIG. 4 illustrates the nucleotide sequence, designated LATK16 (2814 bases), of an IBRV DNA fragment which contains the coding region of the IBRV tk gene and flanking sequences thereof. This sequence is the complement of the DNA strand transcribed to produce IBRV TK messenger RNA. The BglII and SacI(SstI) restriction sites bracket the nucleotide sequences deleted from IBRV(NG) dl TK clone 1. The predicted amino acid sequence of the IBRV TK polypeptide is shown in the 3-letter amino acid code designation.

DETAILED DESCRIPTION OF THE INVENTION

Figure 1:
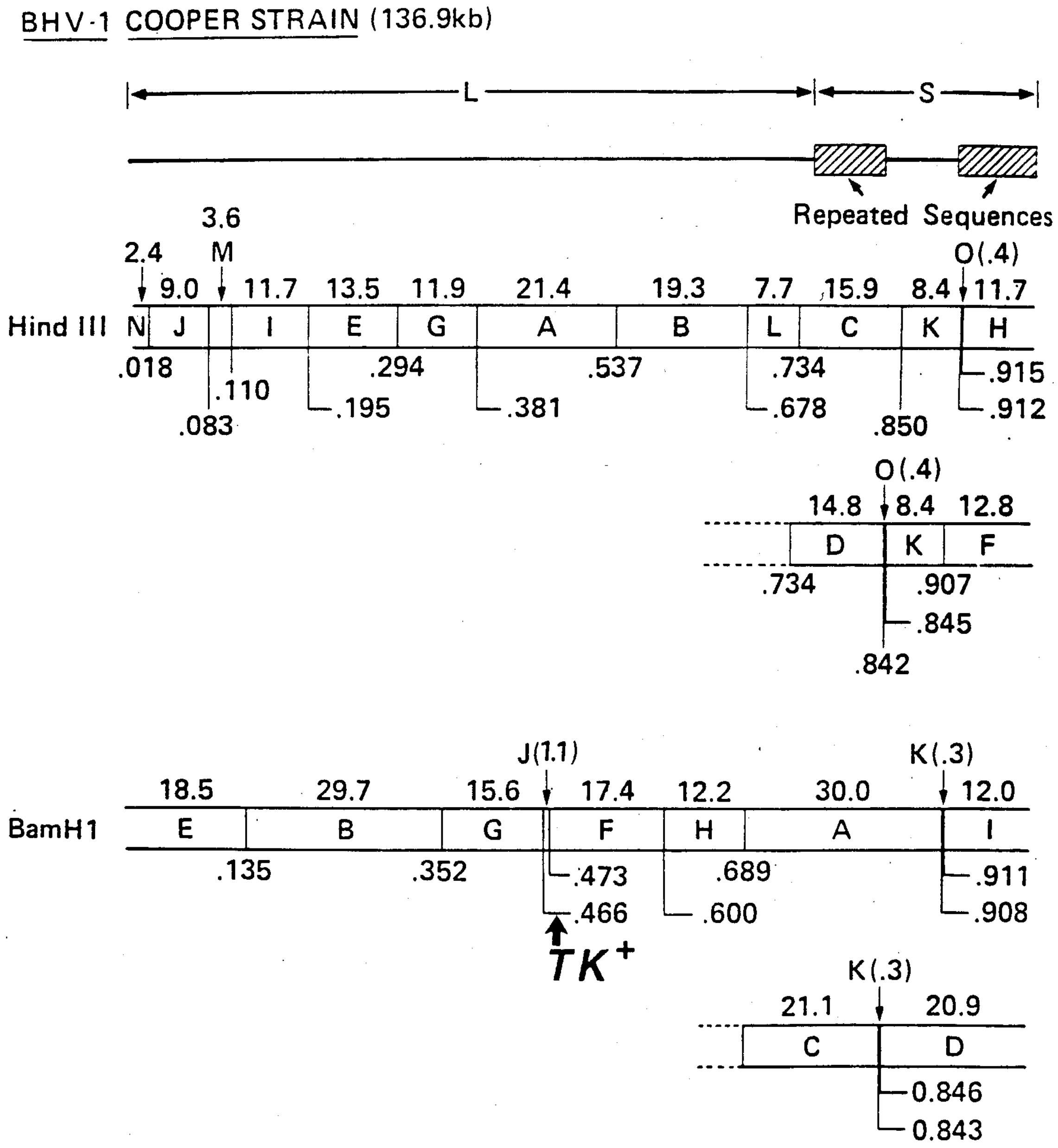
FIG. 1 illustrates IBRV(BHV-1) Cooper strain HindIII BamHI DNA restriction maps. These maps are very similar to those of other strains of IBRV including the Los Angeles strain. The inverted repeat and terminal repeat regions of the DNA are shown as hatched boxes. These regions are present in the short (S) segment of the IBRV genome and bracket the short unique sequences of the DNA. The long unique (L) segment of IBRV DNA is also shown. The IBRV tk gene is located at about 0.47 map units on the IBRV genome, i.e., within the HindIII-A and BamHI-J fragments. DNA fragments are lettered according to size, with kb above each line and fractionated map distances below each line.

The present invention goes beyond a method of merely isolating attenuated tk− IBRV mutants which can be used safely to prevent IBR disease, but relates to IBRV deletion mutants which fail to produce any functional TK enzyme activity and processes for the production and use thereof. Since the mutants lack part of the DNA sequence coding for TK, reversion to tk+ does not occur.

In one embodiment, the present invention comprises a highly attenuated IBRV which fails to produce any functional TK as a result of a deletion in the tk gene, and a MLV vaccine for IBR comprising (1) a pharmaceutically effective amount of said virus, and (2) a pharmaceutically acceptable carrier or diluent.

Another embodiment of the present invention comprises a process for producing a highly attenuated IBRV which fails to produce any functional TK as a result of a deletion in the tk gene comprising:

(1) Constructing a hybrid plasmid comprising a cloning vector and a DNA fragment of IBRV containing substantially all of the IBRV tk gene;

(2) Co-transfecting, in $tk^+$ host cells, the hybrid plasmid of step (1) with infectious DNA from a $tk^-$ IBRV mutagen-induced mutant;

(3) Selecting, in tk− host cells, for tk+ IBRV from the virus produced in step (2);

(4) Deleting DNA sequences from the hybrid plasmid of step (1) such that less than substantially all of the IBRV tk gene is present;

(5) Co-transfecting, in tk+ host cells, IBRV tk30 DNA derived from the tk+ IBRV obtained in step (3) with the resulting tk− hybrid plasmid of step (4); and (6) Selecting, in tk− host cells, for tk− IBRV from the virus produced in step (5) so as to produce tk− IBRV mutants which fail to produce any functional TK as a result of a deletion in the tk gene.

In still another embodiment, the present invention comprises insertion of an oligonucleotide linker in place of the deleted IBRV DNA in step (4) while retaining IBRV DNA sequences adjacent to each side of the deleted IBRV DNA fragments.

In a further embodiment of the present invention, the tk− IBRV mutagen-induced mutant in step (2) is a temperature-resistant mutant such that the resulting mutant in step (6) is both temperature resistant and a tk− deletion mutant.

In an additional embodiment of the present invention, the above-described objects have been met by a process for producing a highly attenuated IBRV which fails to produce any functional TK as a result of a deletion in the tk gene comprising:

(1) Constructing a hybrid plasmid comprising a cloning vector and a DNA fragment of IBRV containing substantially all of the IBRV tk gene;

(2) Co-transfecting, in tk+ host cells, the hybrid plasmid of step (1) with infectious DNA from a tk− IBRV mutagen-induced mutant;

(3) Selecting, in tk− host cells, for tk+ IBRV from the virus produced in step (2);

(4) Deleting DNA sequences from the hybrid plasmid of step (1) such that less than substantially all of the IBRV tk gene is present;

(5) Co-transfecting, in tk+ host cells, IBRV tk+ DNA derived from the tk+ IBRV obtained in step (3) with the resulting tk− hybrid plasmid of step (4);

(6) Selecting, in tk- host cells, for tk- IBRV from the virus produced in step (5) so as to produce tk− IBRV mutants which fail to produce any functional TK as a result of a deletion in the tk gene; and (7) Propagating the resulting IBRV which fails to produce any functional TK as a result of a deletion in the tk gene of step (6) at a non-permissive temperature for a temperature-sensitive virus so as to select for and produce a temperature-resistant IBRV which fails to produce any functional TK as a result of a deletion in the tk gene.

The tk gene is approximately 1500 bp in size. The deletion mutants can be produced by eliminating a 75 to 1500 bp DNA fragment from an appropriate coding region of the tk gene so that proper folding or substrate binding of the TK is prevented. Alternatively, the deletion mutants can be produced by eliminating a 10 to 100 bp DNA fragment so that the proper reading frame of the gene is shifted. In the latter instance, a truncated polypeptide may be produced because polypeptide synthesis is aborted due to a frame shift-induced stop codon. The preferred size of the deletion is about 75 to 750 bp.

As used herein, "flanking sequences" means the sequences upstream, downstream, or both upstream and downstream, from the tk gene coding sequences. The upstream sequences contain the transcriptional control signals, i.e., promoters and enhancers, wherein the downstream sequences contain the transcription termination and polyadenylation signal of the tk gene.

The precise IBRV tk gene sequences which must be present in the hybrid plasmid of step (1) will depend on the sequences chosen for the deletion and the restriction nucleases to be employed in the engineering of the deletion mutant.

The $tk^-$ IBRV mutant employed in this embodiment may also contain one or more mutagen-induced point mutations in the coding region of the tk gene. Therefore, in this instance, the hybrid plasmid to be employed in step (1) must contain $tk^+$ IBRV gene sequences to replace the specific sequences mutated in the $tk^-$ IBRV mutant. Recombination events between the $tk^-$ IBRV DNA and the hybrid plasmid of step (1) have to occur both upstream and downstream from the mutagen-induced point mutation(s) in the $tk^-$ IBRV gene. Although the crossover events, i.e., marker rescue, by which the hybrid plasmid of step (1) replaces the mutated $tk^-$ IBRV DNA might theoretically occur even when the rescuing plasmid IBRV DNA fragment is small, e.g. 50 to 100 bp; in practice, marker rescue by such a small DNA fragment is unlikely. By contrast, the probability of marker rescue is greatly increased when the rescuing DNA fragment is greater than 1.0 kb. Note, the IBRV DNA insert in pLAH-A, described below, is 21.4 kb.

The specific IBRV DNA sequences adjacent to the deletion in the plasmid required in step (4) depend on the specifics of the deletion in the hybrid plasmid. In general, the size of the IBRV DNA sequences adjacent to both the 3′ and 5′ sides of the deletion will be at least about 400 bp. In pLATK dl NdeI dl BglII/NG/SstI, described in detail below, the 3′ and 5′ sequences on both sides of the deletion were 2.3 kb and 1.4 kb in length.

In a second embodiment, the deletion mutants can contain a oligonucleotide linker in place of the deleted IBRV DNA. The oligonucleotide linker is generally 8–10 nucleotides in length, but can be longer, e.g. about 50 nucleotides, or shorter, e.g. 4, 5 or 7 nucleotides. The preferred length of the oligonucleotide linker is about 20 to 40 nucleotides in length. The DNA sequence of the oligonucleotide linker is not critical.

The method of inserting the oligonucleotide into the deletion in the plasmid DNA will depend upon the type of oligonucleotide linker used. Palindromic double stranded linkers containing one or more restriction nuclease sites in the oligonucleotide sequence (New England Biolabs) may be inserted by well known procedures (see: Maniatis, T., Fritsch, E. F., Sambrook, J., *Molecular Cloning,* Cold Spring Harbor Laboratory (1982)). Oligonucleotide linkers may also be inserted into deletions in plasmid DNA by tailing ends with complementary homopolymers using terminal transferase (see: Maniatis, T., Fritsch, E. F., Sambrook, J., *Molecular Cloning,* Cold Spring Harbor Laboratory (1982)). Alternatively, as in the example of the present invention, an oligonucleotide linker may be inserted into a deletion in a plasmid by bridging, through annealing of oligonucleotide containing ends complementary to a cleaved plasmid's 3′-recessed and 3′-protruding cohesive ends, followed by filling in of the gap complementary to the oligonucleotide sequence with DNA polymerase (Klenow's fragment). After subsequent ligation with T4 DNA ligase, closed circular DNA molecules can be regenerated. By the judicious choice of oligonucleotide linker length, frame shift mutations may be produced in the tk gene, augmenting the effect of deletions within the tk gene.

The particular cloning vector employed in the present invention to construct a hybrid plasmid comprising a DNA fragment of IBRV containing the IBRV tk gene and flanking sequences thereof is not critical as long as the cloning vector contains a gene coding for a selective trait, e.g. drug resistance. Examples of such cloning vectors include pBR322 and pBR322-based vectors (see: Sekiguchi, T., Nishimoto, T., Kai, R. and Sekiguchi, M., *Gene* 21:267–272 (1983)), pMB9, pBR325, pKH47 (Bethesda Research Laboratories), pBR328, pHC79, phage Charon 28 (Bethesda Research Laboratories, Boehringer Manneheim Biochemicals), pKB11, pKSV-10 (P-L Biochemicals), pMAR420 (see: Otsuka, H., Hazen, M., Kit, M., Qavi, H. and Kit, S., *Virol.* 113:196–213 (1981)) and oligo (dG)-tailed pBR32(Bethesda Research Laboratories).

pBR322 is the preferred cloning vector employed in the present invention since the IBRV HindIII-A fragment was found, see below, to contain the IBRV tk gene and pBR322 has only one HindIII cloning site. Insertion of a DNA fragment at this site inactivates the cloning vector tetracycline gene, but not the ampicillin gene, so that tetracycline-sensitive, ampicillin-resistant hybrid plasmids that are larger than pBR322 due to the insertion can easily be isolated.

Other cloning vectors containing unique cloning sites which are useful in the present invention can be determined upon evaluation of restriction nucleases other than HindIII which produce fragments containing the IBRV tk gene. Other restriction nucleases which can be employed to produce fragments containing the IBRV tk gene, and thus other cloning vectors which can be useful in the present invention, are readily apparent from the IBRV tk gene sequence and hybrid plasmids shown in FIGS. 2-4 and which are discussed more fully below.

For example, pMB9, pBR325, pKH47, pBR328, pHC79 and phage Charon 28 also have a single HindIII cloning site and can be used to clone the HindIII-A fragment of IBRV. Alternatively, the 3.4 kb PstI fragment of IBRV (map units 0.2 to 3.6 of pLATK dl NdeI, described below) can be cloned at the PstI site of pBR322 or pBR325 with selection of ampicillin-sensitive, tetracycline-resistant transformed bacteria.

Similarly, oligo (dG)-tailed pBR322 can be employed as the cloning vector with an oligo (dC)-tailed HindIII fragment of IBRV.

The specific host employed for growing the plasmids of the present invention is not critical. Examples of such hosts include *E. coli* K12 RR1 (see: Bolivar, F., Rodriguez, R. L., Greene, P. J., Betlach, M. C., Heyneker, H. L., Boyer, H. W., Crosa, J. H., and Falkow, S., *Gene* 2:95–113 (1977)); *E. coli* K12 HB101 (ATCC No. 33694); *E. coli* MM21 (ATCC No. 336780); and *E. coli* DH1 (ATCC No. 33849). *E. coli* K12 RR1 is the preferred host and has an $F^-$ hsd R hsd M genotype.

Similarly, alternative vector/cloning systems could be employed such as plasmid vectors which grow in *E. coli* or *Saccharomyces cerevisiae,* or both, or plasmid vectors which grow in *B. subtilus* (see: Ure, R., Grossman, L. and Moldave, K., *Methods in Enzymology* "Recombinant DNA", vol. 101, Part C, Academic Press, N.Y. (1983)).

The specific tk+ host cells employed in the present invention are not critical so long as they allow for permissive growth of IBRV. Examples of such tk+ host cells include RAB-9 (ATCC No. CRL-1414); primary rabbit kidney cells, secondary rabbit kidney cells; rabbit cornea (SIRC) cells (ATCC No. CCL-60), rabbit kidney (LLC-RK1) cells (ATCC No. CCL-106), embryo bovine trachea (EBTR) cells (ATCC No. CCL-44), bovine turbinate (BT) cells (ATCC No. CRL-1390), and bovine kidney (MDBK) cells (ATCC No. CCL-22). (The American Type Culture Collection Catalog indicates that some types of lamb, goat, cat, and horse cells may also be permissive for IBRV(Los Angeles) (ATCC No. VR-188)). RAB-9 are the preferred tk+ host cells employed in the present invention. However, it should be noted that for the production of virus used for vaccination of animals in the field, a U.S. Dept. of Agriculture certified cell line permissive for IBRV, preferably of the same species as the animal to be vaccinated, and free of other infectious agents, should be used. For example, a suitable bovine cell line would be a certified diploid non-tumorigenic bovine turbinate or kidney cell line free of mycoplasma and other viruses.

The specific tk− host cells employed in the present invention are not critical so long as they allow for permissive growth of IBRV. An example of a tk− host cell which allows permissive growth of IBRV is the rabbit RAB(BU) cell line, which was derived from RAB-9 cells (see: Kit, S. and Qavi, H., *Virol.* 130:381–389 (1983)). Other tk− host cells of rabbit or bovine origin which can be employed in the present invention can be obtained by following, for example, the procedures previously used to isolate tk− mouse, human, and rabbit cell lines (see: Kit, S., Dubbs, D. R., Piekarski, L. J., and Hsu, T. C., *Exptl. Cell Res.* 31:297–312 (1963); Kit, S., Dubbs, D. R., and Frearson, P. M., *Int. J. Cancer.* 1:19–30 (1966); and Kit, S. and Qavi, H., *Virol.* 130:381–389 (1983)). RAB(BU) cells are the preferred tk− host cells employed in the present invention not only because they permit the replication to high titers of both tk+ and tk− IBRV strains, but also because they do not detectably revert to tk+ in selective medium (hypoxanthine, $10^{-4}$M; aminopterin, $10^{-6}$M; thymidin, $4\times10^{-5}$M; and glycine, $10^{-5}$M (hereinafter "HATG medium")) and they can be used for the plaque titration of IBRV at both permissive (about 34.5° C.) and non-permissive (about 39.1° C.) temperatures. It is important that the tk− cells do not detectably revert to tk+ in HATG medium, because reversion to tk+ would interfere with autoradiographic and thymidine plaque autoradiographic assays employed to distinguish the phenotypes of tk+ and tk− viruses and mixtures thereof.

The specific tk− IBRV strain employed in the present invention is not critical and can be either a non-temperature-resistant or a temperature-resistant strain. Examples of such tk− IBRV strains include the non-temperature-resistant, 5-bromovinyldeoxyuridine-resistant IBRV mutant of IBRV(P8-2) (see: Weinmaster, G. A., Misra, V., McGuire, R., Babiuk, J. A., and DeClercq, E., *Virol.* 118:191–301 (1982)) and the temperature-resistant IBRV(B8-D53) (see: Kit, S. and Qavi, H., *Virol.* 130:381–389 (1983); and U.S. patent application Ser. No. 516,179, filed July 21, 1983; ATCC No. VR-2066). IBRV(B8-D53) is the preferred tk− IBRV strain employed in the present invention for the following reasons. First, this mutant was obtained by serial passage of the Los Angeles strain of IBRV in bovine and rabbit cells in the presence of a mutagen, i.e., 5-bromodeoxyuridine, so that multiple genetic alterations have accumulated in the IBRV genome. As a result, the ability of the virus to cause disease is reduced. Second, this strain does not detectably revert to tk+ in vitro in tissue culture or in vivo in calves. Hence, the virus can be used in marker transfer studies for the analysis of IBRV DNA fragments containing the coding region of the tk gene. Third, this strain replicates in permissive cells and over the temperature range of about 30° C. to 40° C., i.e. is temperature resistant. Fourth, pilot experiments in calves and in pregnant cows using this strain have demonstrated the safety and efficacy thereof. That is, as described above, recent studies have demonstrated that IBRV(B8-D53) is highly attenuated, can be administered safely by intramuscular, intranasal, or intravaginal injections to calves and to pregnant cows, and protects these animals from IBR when the calves and pregnant cows are challenge-exposed to the highly virulent Cooper strain of BHV-1.

The specific tk+ IBRV strain employed in the present invention is not critical and can be either non-temperature resistant or temperature resistant. Examples of such tk+ IBRV strains include: the following non-temperature-resistant strains: Los Angeles strain (ATCC No. VR-188), Cooper strain (ATCC No. VR-864), IPV strain K22 (see: Kendrick, J. W., Gillespie, J. H., and McEntee, K., *Cornell Vet.* 48:458–495 (1958)), strains MO3, MO6, BFN-IH, BFN-IIN, BFN-IID, Gi 1 to 5, Bi, B4, BRV, LAE, V3 415, V3 416, V3 18, V3 93 (see: Gregersen, J-P., Pauli, G., and Ludwig, H., Arch. Virol. 1. 84:91-103 (1985)), BFA Wabu strain (see: Ackermann, M. and Wyler, R., *Vet. Microbiol.* 9:53–63 (1984)), strain P8–2 (see: Weinmaster et al., *Virol.* 118:191–201 (1982)), strains Weinmaster et al., *Virol* 118:191–201 (1982)), strains P10, P10, and P34 (see: Engles, M., Steck, F., and Wyler, R., *Arch. Virol.* 67:169–174 (1981)), Alberta (Canada) isolates No. 1 to No. 122 (see: Misra, V., Babiuk, L. A., and Darcel, C. le Q., *Arch. Virol.* 76:341–354 (1983)); or temperature-resistant strains such as IBRV(RTK-1B). The preferred tk+ IBRV strain employed in the present invention is IBRV(RTK-1B). As described in detail below, this strain was obtained by marker transfer of the tk gene from a hybrid plasmid to IBRV(B8-D53) (ATCC No. VR-2066), i.e. a tk− IBRV strain which contains multiple mutations. Thus, IBRV(RTK-1B) retains the multiple mutations of IBRV(B8-D53) and is temperature resistant. IBRV(RTK-1B) differs from IBRV(B8-D53) only in that IBRV(RTK-1B) expresses functional TK and IBRV(B8-D53) does not.

In the context of this invention, a temperature-resistant virus is a virus which is non-temperature sensitive. Thus, a temperature-resistant virus is capable of replicating, at a non-permissive temperature, i.e. about 38.5° C. to 40° C., preferably 39.1° C., about as well as the parental virus or field isolates of IBRV replicate at a permissive temperature. By contrast, temperature-sensitive IBRV strains contain mutations in viral genes essential for replication, whereby functional gene products are produced at permissive temperatures, i.e. about 32° C. to 37.5° C., preferably 34.5° C., but not at non-permissive temperatures. Therefore, in temperature-sensitive viruses, production of infectious virus particles is 4 to 7 logs lower at the non-permissive temperatures compared to production at permissive temperatures. With temperature-resistant virus strains, production of infectious virus particles is about the same at non-permissive temperatures as at permissive temperatures.

Some temperature-sensitive respiratory virus strains, for example, a temperature-sensitive mutant of IBRV, have previously been used as MLV vaccines (see: Pastoret, P. P., Thiry, E., Brocphier, B., and Derboven, G., *Ann. Rech. Vet.* 13:221–235 (1982) and Chanock, R. M., *J. Infect. Dis.* 143:364–374 (1981)). The rationale for such use is that the temperature-sensitive virus can undergo limited replication at privileged sites, such as the upper respiratory tract, and elicit local host immunological responses. However, the temperature-sensitive viruses are impaired in replication in the deeper tissues of the host animal, where the temperature is non-permissive for virus replication.

Temperature-resistant viruses are superior to temperature-sensitive viruses as MLV vaccines because: (1) attenuation results from alterations in specific pathogenic virus genes rather than from crippling viral genes required for replication; and (2) the temperature-resistant virus strains can be administered IM, IN, or intravaginally and can replicate in the deep tissues of the body so as to elicit a more complete and prolonged immunological response.

In contrast, temperature-sensitive viruses only replicate at low-temperature sites, such as the upper respiratory tract and thus can only be administered IN.

The possible selection means employed in steps (3) and (6) are not critical to the present invention and are well known in the art (see: U.S. Pat. No. 4,514,497). For example, in step (3) selection can be carried out using HATG medium and in step (6) selection can be carried out using 5-bromodeoxyuridine (hereinafter "BrdUrd"), 5-iododeoxyuridine, 5-bromovinyldeoxyuridine or arabinosylthymine.

A pharmaceutically effective amount of the above-described MLV of the present invention can be employed along with a pharmaceutically acceptable carrier or diluent as a vaccine against IBR in animals, such as bovine, sheep, goats and swine.

Examples of pharmaceutically acceptable carriers or diluents useful in the present invention include any physiological buffered medium, i.e, about pH 7.0 to 7.4, containing from about 2.5 to 15% serum which does not contain antibodies to IBRV, i.e., is seronegative for IBRV. Agammaglobulin serum is preferred to serum which contains gamma globulin. Examples of serum to be employed in the present invention include swine serum, fetal calf serum, horse serum and lamb serum. Agammaglobulin calf serum is preferred for the vaccination of calves. Agammaglobulin swine serum from pigs seronegative for IBRV is preferred for the vaccination of swine. Serum protein such as porcine albumin or bovine serum albumin (hereinafter "BSA") in an amount of from about 0.5 to 3.0% can be employed as a substitute for the serum. However, it is desirable to avoid the use of foreign proteins in the carrier or diluent which will induce allergic responses in the animal being vaccinated.

The virus may be diluted in any of the conventional stabilizing solutions containing phosphate buffer, glutamate, casitone, and sucrose or sorbose, or containing phosphate buffer, lactose, dextran and glutamate.

It is preferred that the vaccine viruses of the present invention be stored at a titer of at least $10^5$ to $10^6$ PFU/ml at $-70°$ C. to $-90°$ C. or in a lyophilized state at 2° C. to 7° C. The lyophilized virus may be reconstituted for use with sterile distilled water or using an aqueous diluent containing preservatives such as gentamicin and amphotericin B or penicillin and streptomycin.

The useful dosage to be administered will vary depending upon the age, weight and species of the animal vaccinated and the mode of adminstration. A suitable dosage can be, for example, about $10^{4.5}$ to $10^7$ PFU/animal, preferably about $10^{4.5}$ to $10^{5.5}$ PFU.

The vaccines of the present invention can be administered intranasally, intravaginally or intramuscularly. Intramuscularly is the preferred mode of administration.

The following examples are provided for illustrative purposes and are in no way intended to limit the scope of the present invention.

In the following examples, all media and buffer solutions were made up in glass distilled water unless otherwise indicated.

EXAMPLE 1

Construction of Hybrid Plasmids

A. Growth Medium for Tissue Culture Cells

The tk+ host cells (RAB-9) cells were propagated in a temperature-controlled, $CO_2$ incubator, in Eagle's minimum essential medium (hereinafter "APMEM") (Flow Laboratories, Inc.) supplemented with 10% (v/v) bovine fetal serum (hereinafter "BFS") or 10% (v/v) lamb serum, 20 mM bicarbonate, plus 10 mM Hepes (pH 7.3), and 2 mM glutamine plus 50 μg/ml neomycin. This medium will be referred to hereinafter as "growth medium". tk− host cells (RAB(BU)) were grown in the same growth medium as RAB-9 cells, but which was supplemented with BrdUrd (25 μg/ml), except as described below for the passage preceding each experiment.

B. Purification of IBRV DNA

IBRV DNA was prepared essentially as described by Pignatti et al for the preparation of HSV DNA (see: Pignatti, P. F., Cassai, E., Meneguzzi, G., Chemciner, N., and Milanesi, G., *Virol.* 93:260–264 (1979)).

More specifically, 20 8-ounce prescription glass bottle monolayer cultures of RAB-9 cells (about $5\times10^6$ cells/culture) containing 20 ml of growth medium were infected at a multiplicity of infection (hereinafter "m.o.i.") of 5 PFU/cell of IBRV and incubated for 3 hr at 34.5° C., at which time cellular DNA synthesis had been inhibited by the viral infection. Then 1.0 μCi/ml and 0.25 μg/ml of ($^3$H)thymidine was added to radioactively label the viral DNA and incubation was continued at 34.5° C. for 17 hr more. The cells were dislodged from the glass by scraping into the growth medium with a rubber policeman, centrifuged at $600\times g$, washed with ice cold phosphate-buffered saline solution comprising 0.14M NaCl, 0.003M KCl, 0.001M $CaCl_2$, 0.0005M $MgCl_2$, and 0.01M phosphate, pH 7.5 (hereinafter "PBS"), containing 10 μg/ml non-radioactive thymidine. Next, the cells were centrifuged at $600\times g$ and then frozen in an ethanol-dry ice bath.

After thawing, the cell pellet (about 0.7 ml) was resuspended in 9 volumes of lysing solution comprising 0.25% (w/v) Triton X-100, 10 mM EDTA, 10 mM Tris-HCl, pH 7.9. Next, the cell suspension was transferred to a Dounce homogenizer, and incubated at room temperature for 20–30 min with gentle mixing.

Then, the cell suspension was transferred to a glass centrifuge tube and NaCl was added to a final concentration of 0.2M. Next, the tube was inverted several times, and the solution was immediately centrifuged at 1000×g at 4° C. for 10 min.

The resulting supernatant was decanted into a glass tube and deproteinized by incubating with 100 μg/ml proteinase K (E. M. Science) in buffer solution comprising 10 mM Tris-HCl, pH 7.5, 1.0 mM EDTA (hereinafter "TE buffer") for 1 hr at 37° C. Then, 1 volume of 90% (v/v) redistilled phenol was added, the solution was mixed by inversion, centrifuged at 20,000×g, and the aqueous phase, i.e., top phase, was transferred to a polyallomer centrifuge tube. Solid sodium acetate was then added to a concentration of 4.0% (w/v), the nucleic acids were precipitated with 2 volumes of ice cold ethanol, and incubated overnight at −20° C. Thereafter, the precipitate was collected by centrifugation at 16,000 rpm at 4° C. in a Spinco SW25 rotor, dissolved in 2.0 ml TE buffer, and dialyzed at 4° C. against TE buffer.

The resulting DNA solution was then transferred to a polyallomer centrifuge tube and CsCl in TE buffer was added to 57% (w/w) ($\rho$=1.715 g/cm$^2$). Next, the DNA was centrifuged for 46 hr at 22.5° C. at 44,000 rpm in a Spinco No. 50 Ti rotor. Then, 12 drop fractions were collected from the bottom of the polyallomer tube and aliquots of 4.0 μl were counted in a liquid scintillation spectrometer to locate the IBRV DNA containing fractions ($\rho$=about 1.727 g/cm$^2$). When a total of 25 fractions were collected, generally fractions 13–15 contained the IBRV DNA.

The IBRV DNA-containing fractions were then pooled and dialyzed against several changes of TE buffer at 4° C. for about 24 hr. The concentration of DNA was determined fluorometrically. The IBRV DNA yield was about 25 μg from $10^8$ cells The identity of the IBRV DNA was verified by the pattern of restriction nuclease-digested IBRV DNA fragments obtained after electrophoresis at 4° C. in a submarine gel apparatus (Bethesda Research Laboratories, Inc.) as described below.

More specifically, DNA was cleaved with BamHI, SalI, KpnI, or HindIII restriction nucleases under the reaction conditions recommended by the manufacturer (New England BioLabs, Inc.). Next, 1/10 volume of a solution comprising 0.4% (w/v) bromphenol blue, 125 mM EDTA, and 50% (v/v) glycerol was added to terminate the reaction, followed by heating at 65° C. for 10 min. 20 μl aliquots of each sample was applied into the sample wells of the agarose gel and electrophoresis was carried out as described below.

Electrophoresis of restriction nuclease fragments was carried out on 0.6% (w/v) agarose slab gels (see: Kit, S., Qavi, H., Dubbs, D. R., and Otsuka, H.. *J. Med. Virol.* 12:25–36 (1983)) in electrophoresis buffer comprising 30 mM $NaH_2PO_4$, 1.0 mM EDTA, 40 mM Tris-Base, pH 8.1 (hereinafter "electrophoresis buffer") at 45 volts, 4° C. for about 16 hr. After electrophoresis, DNA fragments were stained by soaking the gel in electrophoresis buffer containing 0.5 μg/ml ethidium bromide, visualized over a long wave UV illuminator, and photographed. The restriction nuclease maps for the HindIII and BamHI fragments of BHV-1(IBRV) strain (Cooper) are shown in FIG. 1.

IBRV DNA prepared in this manner had an infectivity of about 100 to 1000 PFU/μg DNA in the standard transfection assay.

C. Cloning of the IBRV DNA

The HindIII fragments of DNA from IBRV(Los Angeles) were cloned at the HindIII cleavage site of pBR322 by the following procedure.

4.0 μg DNA from IBRV(Los Angeles) was dissolved in cutting buffer comprising 50 mM NaCl, 50 mM Tris-HCl (pH 8.0), 10 mM $MgCl_2$, and 100 μg/ml BSA (hereinafter "HindIII cutting buffer"). The DNA was then digested at 37° C. for 1 hr with 40 units of HindIII enzyme (New England BioLabs, Inc.). The reaction was terminated by adding an equal volume of 90% (v/v) redistilled phenol, mixing, and centrifuging for phase separation. After dialysis of the aqueous phase against 1×TE buffer, sodium acetate was added to 0.1M followed by the addition of 2 volumes of ethanol, and the DNA precipitate was stored at −20° C. overnight. The DNA precipitate was collected by centrifugation and dissolved in 1×TE buffer.

The restriction nuclease fragments were then combined in the following manner with pBR322 which had been cleaved with HindIII and dephosphorylated:

4.0 μg of HindIII-cleaved IBRV(Los Angeles) DNA was mixed with 0.5 μg of HindIII digested and dephosphorylated pBR322 DNA (New England BioLabs, Inc.), in 0.05 ml of a solution comprising 50 mM Tris-HCl (pH 7.8), 10 mM $MgCl_2$, 20 mM dithiothreitol, 1.0 mM ATP, and 50 μg/ml BSA (hereinafter called "ligation buffer"), and 1000 units of phage T4 DNA ligase (New England BioLabs, Inc.), and incubated overnight at 4° C. The reaction was terminated by adding EDTA to 20 mM and heating at 65° C. for 10 min.

The hybrid plasmid DNA was diluted in TE buffer and used to transform *E. coli* K12 RR1 bacteria as described below (see: Bolivar, F., Rodriguez, R. L., Green, P. J., Betlach, M. C., Heyneker, H. L., Boyer, H.W., Crosa, J.H., and Falkow, S., *Gene* 2:95–113 (1977)).

Bacteria were prepared for transformation using $CaCl_2$ (see: Mandel, M. and Higa, A., *J. Mol. Biol.* 53:159–162 (1970)). Specifically, an overnight culture at a density of 2.0 ($A_{600}$) of *E. coli* K12 RR1 was used to inoculate 200 ml of broth comprising 1.0% (w/v) bactotryptone, 0.5% (w/v) yeast extract, and 0.5% (w/v) NaCl (hereinafter "ML broth"), at a bacterial density of 0.02 ($A_{600}$). The bacteria were incubated for about 2 hr until a density of about 0.5 ($A_{600}$) was achieved. The bacteria were then pelleted by centrifugation and resuspended in ¼ volume of cold 50 mM $CaCl_2$. After a 5 min incubation on ice, the bacteria were again pelleted and resuspended in 1/40 the volume of ice cold 50 mM $CaCl_2$.

Next, 0.1 ml of the hybrid plasmid DNA, about 10–100 ng, in TE buffer was added to 0.2 ml of the $CaCl_2$-treated bacteria. The mixture was kept at 4° C. for 30 min. Then, the temperature was raised to 37° C. for 5 min and 0.3 ml of ML broth was added. Thereafter, incubation was continued for 45 min at 37° C. with gentle shaking. Samples were plated on trypticase soy agar plates (BBL Microbiology Systems) supplemented with 30 μg/ml ampicillin.

Rapid screening of the resulting clones for the desired hybrid plasmid DNA (hereinafter called "rapid screening procedure") was conducted as follows:

An overnight culture of bacteria containing hybrid plasmid DNA was inoculated into 5.0 ml of ML broth containing 30 μg/ml ampicillin and incubated at 37° C. to a density of about 1.5 ($A_{600}$). One ml of this bacterial culture was then transferred to a 1.5 ml Eppendorf polypropylene tube and centrifuged in an Eppendorf centrifuge for about 1 minute at room temperature to pellet the bacteria. Next, the bacteria were resuspended in 0.1 ml of lysozyme solution No. 1 comprising 2.0 mg/ml egg lysozyme; 50 mM glucose; 10 mM cyclohexanediamine tetraacetate (hereinafter "CDTA"); and 25 mM Tris-HCl buffer, pH 8.0 (hereinafter "lysozyme solution No. 1") and then incubated for 30 min at 4° C. Next, 0.2 ml of 0.2N NaOH plus 1.0% (w/v) sodium dodecylsulfate was added to the bacterial suspension and the tube was vortexed and kept at 4° C. for 5 min. Thereafter, 0.15 ml of 3.0M sodium acetate, pH 4.8, was added, and the tube was gently inverted, during which time a "clot" of DNA formed. The DNA was kept at 4° C. for 1 hr to allow chromosomal DNA, protein, and high molecular weight RNA to precipitate. Next, the precipitate was centrifuged in an Eppendorf centrifuge for 5 min at room temperature and the clear supernatant fluid, approximately 0.4 ml, containing recombinant plasmid DNA was transferred to a second Eppendorf centrifuge tube. Then, 2½ volumes of ethanol (approximately 1.0 ml) were added to the second tube which was placed at −20° C. for 30 min. The precipitated hybrid plasmid DNA was collected by centrifugation for 2 min at room temperature in an Eppendorf centrifuge. Then, the hybrid plasmid DNA was dissolved in 0.1 ml of 0.1M sodium acetate, 0.05M Tris-HCl, pH 8.0, reprecipitated with ethanol, collected by again centrifuging, and finally dissolved in 100 μl of 0.1×TE buffer.

Then, a 10 μl aliquot of hybrid plasmid DNA was diluted in 50 μl HindIII cutting buffer and 2.0 units of HindIII were added. Following a digestion period of 60 min at 37° C., the sample was mixed with 1/10 volume of a solution comprising 0.4% (w/v) bromphenol blue, 125 mM EDTA, and 50% (v/v) glycerol, and about 20 μl was applied to a 0.6% (w/v) agarose slab gel for electrophoretic analysis as described above. This analysis revealed whether the hybrid plasmid contained a HindIII insert and, if so, the size, in kb, of the insert (see: Birnboim, H. C. and Doly, J., *Nucl. Acids Res.* 7:1513–1523 (1973)).

Figure 2:
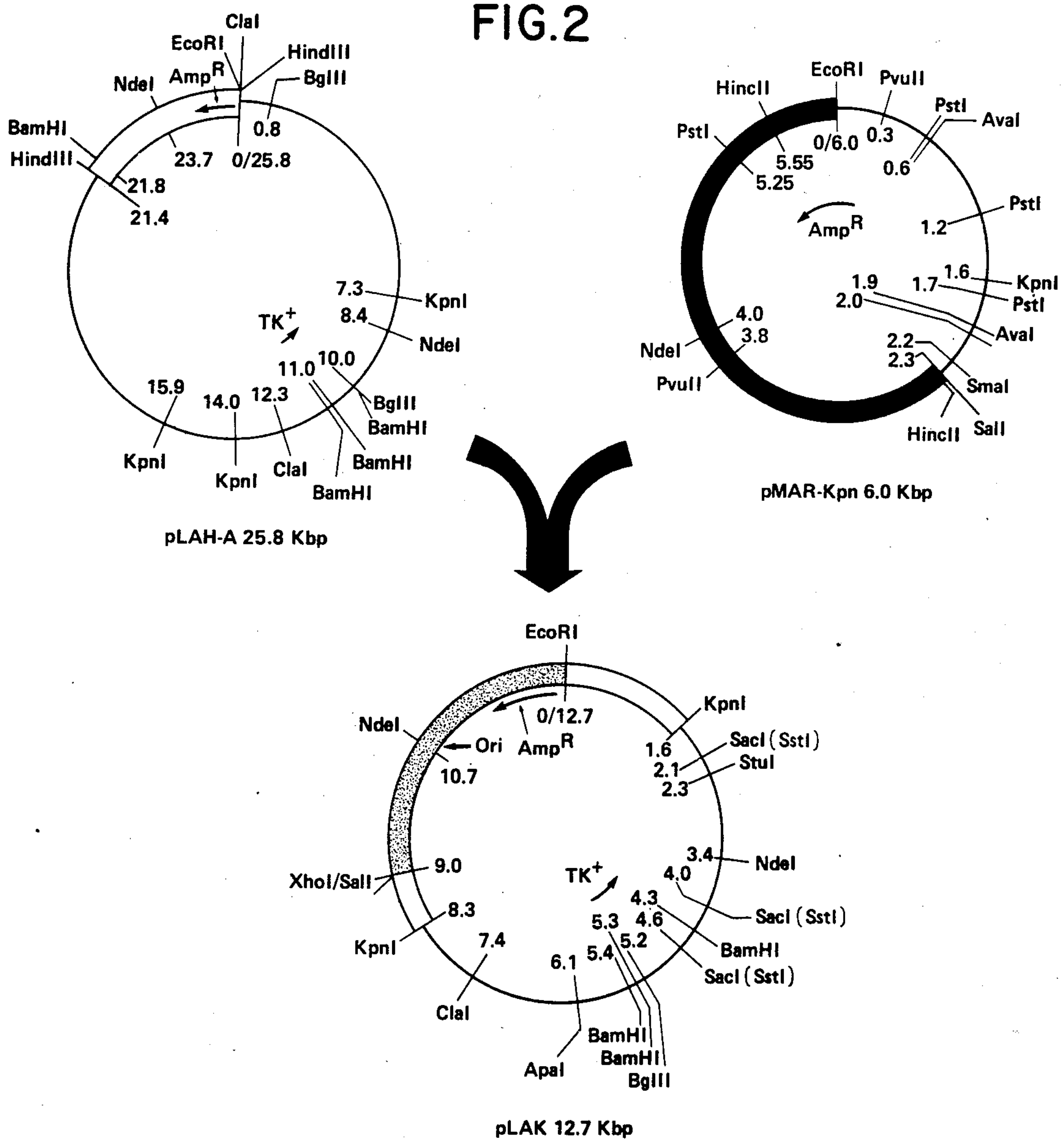
FIG. 2 schematically illustrates, by example, the restriction endonuclease maps of hybrid plasmids containing a functional IBRV tk gene. Plasmid pLAH-A was derived by inserting the 21.4 Kbp HindIII-A fragment of the Los Angeles strain of IBRV (see FIG. 1 for HindIII restriction map) into the HindIII restriction site of bacterial plasmid, pBR322 which is 4.4 Kbp in size. Plasmid pBR322 is tetracycline-resistant (tetR) and ampicillin-resistant (amR). The insertion inactivates the tetR gene, so that $amp^R$, tetracycline-sensitive plasmids, like pLAH-A, can be isolated. Hybrid plasmid pMAR-Kpn is a derivative of plasmid pMAR420 and contains a unique KpnI cloning site (see: Otsuka, H., Hazen, M., Kit, M., Qavi, H., and Kit, S., *Virol.* 113:196–213 (1981)). The black bar and solid line represent, respectively, pBR322 and *Herpesvirus tamarinus* nucleotide sequences. Hybrid plasmid pLAK was obtained by transferring the 6.7 Kbp KpnI fragment of IBRV DNA from pLAH-A to the unique KpnI site of pMAR-Kpn, thereby shortening the cloned IBRV DNA sequence by 14.7 Kbp.

In this manner, a 25.8 Kbp plasmid containing a 21.5 Kbp HindIII insert, which comigrated with the IBRV HindIII-A fragment in agarose gel electrophoresis, was isolated and designated pLAH-A (see FIG. 2).

For large-scale preparation of hybrid plasmid DNA, 200 times the amount of plasmid-transformed bacteria were processed as compared with the bacteria used to produce hybrid plasmid DNA for the rapid screening procedure described above, except that after the first ethanol precipitation, the sample was treated at 37° C. for 30 min, with 0.5 mg of pancreatic RNase A (Worthington Biochemical Corp.) from a stock solution comprising 1.0 mg/ml RNase A in 5.0 mM Tris-HCl, pH 8.0, which had been heated at 100° C. for 10 min. The treatment was followed by the addition of 500 μg of proteinase K (E. M. Science) in TE buffer at 37° C. for 30 min. Subsequently, an equal volume of phenol was added, and the sample was vortexed and centrifuged as described above to separate the phases. The aqueous phase was then removed, precipitated with ethanol, and collected by centrifugation as described above. The precipitate was then dissolved in 0.2 ml of TE buffer and layered on a 10.4 ml linear 10-40% (w/v) sucrose gradient in 50 mM NaCl, 10 mM Tris-HCl, pH 7.5, 1.0 mM EDTA, and was then centrifuged at 4° C. for 20 hr at 24,000 rpm in a Spinco SW41 rotor. 15 drop fractions were collected from the bottom of polyallomer centrifuge tubes into wells of plastic trays. A total of 35 fractions was obtained. 5 μl aliquots were then screened by employing agarose gel electrophoresis as described above. Fractions containing hybrid plasmid DNA were pooled, dialyzed against 0.1×TE buffer, and stored at 4° C. for further studies.

D. Identification by Marker Transfer of the IBRV Fragment Encoding the tk Gene

Homologous recombination in animal cells between purified viral DNA fragments, or by viral DNA fragments amplified by cloning in plasmid vectors, and genomic viral DNA has been used to rescue mutant sequences in either the DNA fragment or the viral genome. The procedure, known as "marker rescue" or "marker transfer", has been employed to map spontaneous mutations and mutations induced by mutagens in the entire viral DNA, as well as to "transfer" mutations from hybrid plasmids into genomic viral DNA (see: Matz, B., Subak-Sharpe, J. H., and Preston, V. G., *J. Gen. Virol.* 64:2261–2270 (1983)).

Marker transfer procedures were used to identify the IBRV(Los Angeles) HindIII fragment which encodes the tk gene. That is, a mixture of infectious IBRV(B8-D53) DNA and candidate hybrid plasmids containing different inserts of IBRV HindIII fragments were cotransfected into RAB-9 cells by the calcium phosphate precipitate method (see: Graham, F. L. and Van der Eb., A. J., *Virol.* 52:456–467 (1973)). Specifically, the following sterile solutions were added to a test tube in sequential order:

(1) 0.02 ml of a 100 μg/ml solution of IBRV(B8-D53) DNA in TE buffer;

(2) 0.4 ml of a 10 μg/ml solution of recombinant plasmid containing various IBRV(Los Angeles) HindIII fragments in 0.1×TE buffer;

(3) 0.25 ml of water;

(4) 0.2 ml of a 100 μg/ml solution of carrier mouse fibroblast (LM(TK−)) cell DNA in TE buffer;

(5) 0.125 ml of 2.0M $CaCl_2$; and (6) 1.0 ml of a 2× balanced salt solution comprising 280 mM NaCl, 1.5 mM $Na_2HPO_4$, 50 mM Hepes, pH 7.12 (hereinafter "2×BSS")

The resulting solution was mixed by inversion and kept at room temperature for 30 min while a DNA-calcium phosphate precipitate formed. Then, 0.5 ml of the suspension containing precipitated DNA-calcium phosphate was added directly to 5.0 ml of growth medium and plated on RAB-9 cells which had been seeded in 60 mm plastic Petri dishes 36 hr earlier. The cells were incubated at 37° C. for 5 hr. Then, fresh growth medium was added and the cultures were further incubated at 34.5° C. for 2–3 days until extensive cytopathic effects occurred. Virus harvests were made as described above.

The harvests of the above transfections were analyzed by thymidine plaque autoradiography for the presence and proportion of tk+ IBRV rescued from IBRV(B8-D53) by pLAH-A (see: Tenser, R. B., Jones, J. C., Ressel, S. J., and Fralish, F. A., *J. Clin. Microboil.* 17:122–127 (1983)) as follows:

100 mm plastic tissue culture grade Petri dishes were seeded with $1.25\times10^6$ RAB(BU) cells in 10 ml of APMEM+10% (v/v) BFS and incubated at 37° C. in a humidified $CO_2$ incubator until the monolayer was semiconfluent (2 to 3 days). Then the medium was removed by aspiration, and 0.5 ml of thawed and sonicated virus samples in growth medium was added at 100 to 1000 PFU/dish and absorbed to the monolayers at 37° C. for 1 hr. The dishes were overlayed with 10 ml of 0.5% (w/v) methyl cellulose in growth medium and incubated at 37° C. for 3 days. The methyl cellulose overlay was removed by aspiration; then the monolayers were rinsed with a solution comprising 8.0 g NaCl, 0.4 g KCl, 0.1 g glucose and 0.02 g phenol red per liter of water (hereinafter called "GKN") followed by the addition of 5.0 ml of growth medium containing 3 μCi of (methyl-$^{14}$C)thymidine (53-59 mCi/mmole) to each dish. At the end of a 6 hr incubation at 37° C., the medium was removed and the monolayers were rinsed with GKN and methanol, and then fixed with methanol for 1 min at room temperature. The monolayers were subsequently washed two times for 5 min each with 5% (w/v) trichloroacetic acid containing 10 μg/ml nonradioactive thymidine, three times for 5 min each with 70% (v/v) ethanol, two times for 5 min each with 90% (v/v) ethanol, and two times for 5 min each with 100% ethanol, all at 4° C. The monolayer was dried, and 5.0 ml of 0.1% (w/v) crystal violet in water was added for 5 min followed by rinsing with tap water and drying at room temperature. The bottoms of the plates were cut out, mounted on cardboard, and placed in a folder with Fuji X-ray film and exposed at −70° C. for 3 days. The film was developed, and the number of dark rim circles representing isotope incorporation by tk+ plaques were counted and compared to the number of total plaques visible on the crystal violet stained monolayers. As shown in Table 1 below, the tk− mutation of IBRV(B8-D53) was efficiently rescued by pLAH-A that contained the IBRV HindIII-A fragment. In contrast, hybrid plasmids that contained the IBRV HindIII-G and HindIII-B fragments, which map on either side of the HindIII-A fragment (see FIG. 1), did not rescue the tk− mutation of IBRV(B8-D53). These results demonstrated that the HindIII-G and HindIII-B fragments do not contain sequences covering the mutation site on the IBRV(B8-D53) tk gene.

TABLE 1

Marker Transfer of IBRV tk+ Gene from Hybrid Plasmid pLAH-A to IBRV(B8-D53)

| Group | DNA used for transfection | IBRV titer after transfection (PFU/ml) | tk+/tk− by autoradiography |
|---|---|---|---|
| I | IBRV(B8-D53) DNA only (control) | $1\times10^5$ | 0/300 |
| II | IBRV(B8-D53) DNA plus plasmid pLAH-A DNA | $2\times10^6$ | 50/57 |

To enrich for recombinant tk+ viruses, the harvests of transfections with platk de Nde I were passaged in RAB(BU) cells, i.e., tk− cells (see: Kit, S. and Qavi, H., *Virol.* 130:381-389 (1983)) in growth medium containing HATG (see: Littlefield, J. W., *Science* 145:709-710 (1964); Littlefield, J. W., *Biochim. Biophys. Acta* 95:14-22 (1965); and Szybalska, E. H. and Szybalski, W., *Proc. Nat. Acad. Sci. USA,* 48:2026-2034 (1962)) as follows:

The virus harvests of the transfection in RAB-9 cells were sonicated and diluted 1:500 in growth medium containing HATG, and confluent monolayer cultures of RAB(BU) were inoculated with virus at an m.o.i. of about 0.01. After a 1 hr absorption at 37° C., fresh growth medium containing HATG was added and the infection was allowed to progress for 48 hr at 34.5° C., at which time virus harvests were again made. A second selection step was conducted in the same manner, except that the virus was diluted 1:5000. The harvested virus from the second selection passage was plaque-purified in RAB-9 cells (see: Kit, S. and Qavi, H., *Virol.* 130:381-389 (1983) and Kit, S., Qavi, H., Dubb's, D. R., and Otsuka, H., *J. Med. Virol.* 12:25-36 (1983)). The resulting plaque-puriified viruses were analyzed by thymidine plaque autoradiography to verify their tk+ phenotype and designated IBRV(RTK-1A) and IBRV(RTK-1B). Then, virus working pools were prepared in RAB-9 cells. The titers of these working pools were about $5\times10^7$ PFU/ml.

Additional marker transfer experiments were carried out, as described above, with infectious IBRV(B8-D53) DNA and plasmids pLATK (described below) and pLATK dl NdeI (described below) (see FIG. 3). These experiments demonstrated that IBRV(B8-D53) was efficiently rescued both by pLATK and by pLATK dl NdeI. These results indicate that the nucleotide sequences for IBRV tk gene expression were present within the 4.1 Kbp IBRV fragment of pLATK dl NdeI.

To confirm that IBRV(RTK-1A) and IBRV(RTK-1B) were indeed IBRV strains, DNA was prepared, as described previously, cleaved with restriction endonucleases, and analyzed by agarose gel electrophoresis. The HindIII and BamHI restriction nuclease patterns were similar to those obtained with the Los Angeles and Cooper strains of IBRV.

E. Subcloning of pLAH-A: Construction of pLAK

A 6.7 Kbp KpnI restriction fragment from pLAH-A was cloned into the KpnI site of pMAR-Kpn. pMAR-Kpn (see FIG. 2) is a 6.0 kb plasmid derived from pMAR420 with a single KpnI cleavage site (see: Otsuka, H., Hazen, M., Kit, M., Qavi, H., and Kit, S., *Virol.* 113:196-213 (1981)). pMAR-Kpn was obtained by deleting the 4.3 XhoI to SalI fragment from pMAR420 (see FIG. 2). Any other plasmid with a single KpnI cleavage site would be equally suitable in the following procedure such as pUC18 and pUC19 (Bethesda Research Laboratories) or pKB11 (Pharmacia, Inc.).

Both plasmids were linearized by cleaving 1.0 μg of pLAH-A and 0.1 μg of pMar-Kpn with 20 units of KpnI in a cutting buffer comprising 6.0 mM NaCl, 6.0 mM Tris-HCl (pH 7.5), 6.0 mM $MgCl_2$, 1.0 mM dithiothreitol, 100 μg/ml BSA (hereinafter "KpnI cutting buffer") during a 1 hr incubation at 37° C. The reaction was stopped by adding CDTA to a final concentration of 20 mM and heating at 65° C. for 30 min. Sodium acetate was added to 0.3M. Then 2 volumes of ethanol was added and the mixture was stored at −20° C. overnight to allow complete precipitation of DNA. The DNA precipitate was collected by centrifugation. The KpnI cleaved pLAH-A and pMAR-Kpn plasmid DNAs were dissolved in ligation buffer and then ligated together by T4 DN ligase, as described previously. *E. coli* K12 strain RR1 was then transformed with the resulting plasmids, as described previously, and the plasmid DNA of recombinant clones was isolated by the rapid screening procedure described above.

The plasmid DNAs of candidate recombinants were treated with KpnI in the KpnI cutting buffer and analyzed by agarose gel electrophoresis as described previously for HindIII. A 12.7 Kbp plasmid with a 6.0 Kbp pMAR-Kpn fragment and a 6.7 Kbp KpnI fragment derived from pLAH-A was obtained and designated pLAK. The large-scale preparation of plasmid pLAK DNA was then carried out as described above.

F. Subcloning of pLAK: Construction of pLATK

Figure 3:
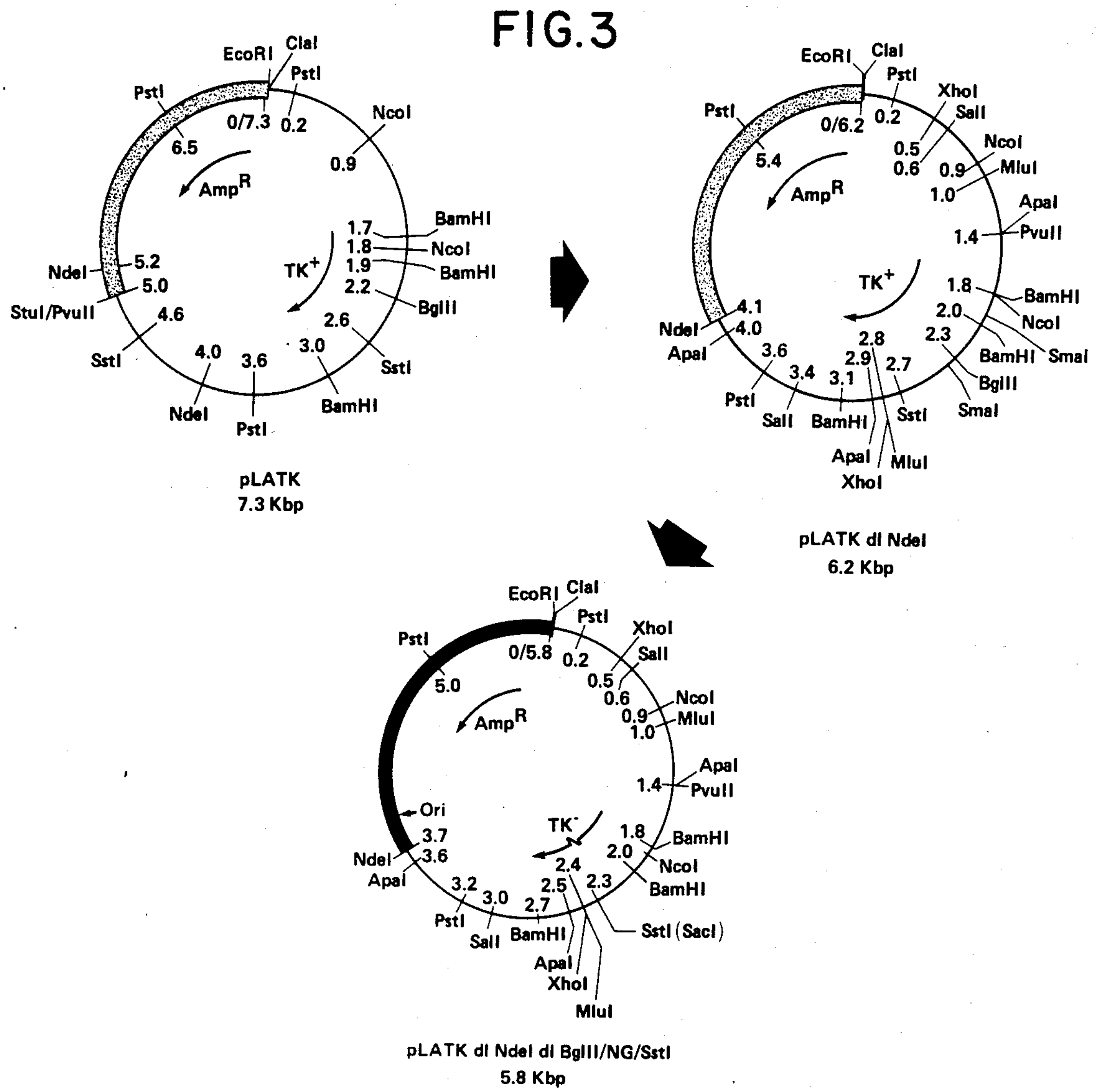
FIG. 3 schematically illustrates, by example, derivation of additional tk+ and tk− plasmids employed in the present invention. Hybrid plasmid pLATK was derived by StuI and ClaI restriction nuclease cleavage of pLAK and ligation of the excised 5.1 Kbp StuI/ClaI fragment to the ClaI/PvuII (2.3 kb) fragment of pBR322, which contains the ampR gene. Plasmid pLATK dl NdeI was derived from pLATK by deletion of the 1.2 kb NdeI sequence of pLATK (4.0 to 5.2 map units). Plasmid pLATK dl NdeI dl BglII/NG/SstI was derived from pLATK dl NdeI by: (i) deleting the 400 bp BglII/SstI sequence (2.3 to 2.7 map units), and then (ii) ligating a linker (a 40 bp oligonucleotide which contains 5′-GATCT-3′ (BglII) and 5′-GAGCT-3′ (SstI) cohesive termini) to the large fragment of BglII/SstI-cleaved pLATK dl NdeI, so as to produce a closed-circular hybrid plasmid of 5.8 Kbp. Plasmid pLATK dl NdeI dl BglII/NG/SstI was used in marker transfer experiments with tk+ IBRV DNA to obtain an example of the present invention, i.e. IBRV(NG) dl TK clone 1.

The 5.1 Kbp StuI to ClaI IBRV DNA fragment of pLAK was cloned into the PvuII to ClaI cleavage sites of pBR322 (see FIGS. 2 and 3). More specifically, 10 μg of pLAK was added to a reaction buffer comprising 100 mM NaCl, 10 mM Tris-HCl (pH 8.0), 10 mM $MgCl_2$, 6.0 mM 2-mercaptoethanol, and 100 μg/ml BSA. The DNA was digested for 1 hr at 37° C. with 16 units of StuI. The reaction was terminated by adding CDTA to 20 mM and heating at 65° C. for 30 min. Sodium acetate was added to 0.15M and the DNA precipitated with 2 volumes of ethanol. The DNA precipitate was collected by centrifugation, then redissolved in ClaI cutting buffer comprising 50 mM NaCl, 6.0 mM Tris-HCl (pH 7.9), 6.0 mM $MgCl_2$, 100 μg/ml BSA (hereinafter called "ClaI cutting buffer). The StuI cleaved pLAK was digested for 1 hr at 37° C. with 8 units of ClaI. The reaction was terminated and the DNA collected by ethanol precipitation as described above.

0.3 μg of pBR322 was added to a cutting buffer comprising 60 mM NaCl, 6.0 mM Tris-HCl (pH 7.5), 6.0 mM $MgCl_2$, 6.0 mM 2-mercaptoethanol, and 100 μg/ml BSA. 5 units of PvuII was then added and the DNA digested for 1 hr at 37° C. The reaction was terminated and the DNA ethanol precipitated and collected as above. The PvuII cleaved pBR322 was dissolved in ClaI cutting buffer and digested with 4 units of ClaI for 1 hr at 37° C. The reaction was terminated and the DNA ethanol precipitated and collected as above.

The ClaI and StuI cleaved pLAK along with the PvuII and ClaI cleaved pBR322 was combined in ligation buffer and ligated by adding 1000 units of T4 DNA at 4° C. overnight. The reaction was terminated and transformation of *E. coli* K12 RR1 carried out as described previously.

Rapid screening as described above resulted in the identification of a plasmid, designated pLATK which had the 5.0 Kbp StuI to ClaI fragment of pLAK cloned into the PvuII to ClaI sites of pBR322 (see FIG. 3). Working pools of plasmid pLATK DNA were then prepared as described above.

G. Subcloning of pLATK: Construction of pLATK dl NdeI

The 1.2 Kbp NdeI fragment of pLATK (4.0 to 5.2 map units, see FIG. 3) was deleted by mixing 0.03 μg of pLATK DNA in a cutting buffer comprising 150 mM NaCl, mM Tris-HCl (pH 7.8), 7.0 mM $MgCl_2$, 6.0 mM 2-mercaptoethanol, 100 μg/ml BSA (hereinafter called "NdeI cutting buffer"). The DNA was then digested for 1 hr at 37° C. with 2 units of NdeI. The reaction was terminated by adding CDTA to 20 mM and heating at 65° C. for 30 min. Sodium acetate was added to 0.1M, and 2 volumes of ethanol was added followed by storage at −20° C. overnight. The DNA precipitate was collected by centrifugation, then dissolved in ligation buffer. The NdeI cleaved pLATK was religated with T4 DNA ligase as described previously followed by transformation of *E. coli* K12 strain RR1 and rapid screening of plasmid DNAs as described previously. The plasmid DNAs of candidate deletion recombinant hybrids were treated with NdeI in NdeI cutting buffer and analyzed by agarose gel electrophoresis as described previously. A 6.2 Kbp plasmid containing only one NdeI cleavage site was isolated and was designated as pLATK dl NdeI (see FIG. 3).

Construction of Plasmid pLATK dl NdeI dl BglII/NG/SstI

The 0.4 Kbp BglII to SstI fragment of pLATK dl NdeI (see FIG. 3) was excised from 1.0 μg of the plasmid by first incubating the DNA with 8 units of SstI for 1 hr at 37° C. in SstI cutting solution comprising 50 mM Tris-HCl (pH 8.0), 10 mM MgC12, 50 mM NaCl. Then the salt concentration was increased to 100 mM NaCl and 8 units of BglII was added. Incubation was continued for an additional hour. The reaction was stopped by adding CDTA to a final concentration of 20 mM and heating the mixture at 65° C. for 30 min. The DNA was ethanol precipitated and collected by centrifugation as described previously.

The BglII to SstI ends of the plasmid were bridged with a 40-mer oligonucleotide linker having the following sequence:

(5'-GATCTATGAATCAGGTCGCAGG-
CGAGAATGAGTAAGAGCT-3')

(hereinafter "NG linker"). The NG linker was synthesized by phosphoramidite chemistry on an automated DNA synthesizer (Systec, Inc.) according to the manufacturer's instructions. The BglII and SetI cleaved pLATK dl NdeI plasmid DNA was annealed at 65° C. for 45 min to 8.7 μg of the NG linker in an 18 μl reaction mixture comprising 6.6 mM Tris-HCL (pH 7.5), 6.6 mM $MgCl_2$, 1.1 mM dithiothreitol, 55 mM NaCl, followed by slow cooling at 4° C. in a refrigerator. The single stranded oligonucleotide bridged the cohesive BglII and SstI ends of the plasmid. The gapped sequence complementary to the NG linker was filled by adding 1.0 μl of a solution of 2 mM each of dATP, dGTP, TTP, dCTP, and 1.0 μl (2 units) of *E. coli* DNA polymerase, Klenow fragment (Bethesda Research Laboratories)) and incubating 1 hr at 22° C., followed by heat inactivation at 70° C. for 5 min. Ligation of the ends was accomplished by adding 5.0 μl of 10 mM ATP, 25 μl of 100 mM Tris, pH 7.8, 20 mM $MgCl_2$, 40 mM dithiothreitol, 100 μg/ml BSA and 1000 units of T4 ligase, and then incubating at 4° C. overnight. The ligation reaction was terminated by adding 3.0 μl of 0.25M EDTA and heating at 65° C. for 30 min.

The ligation mixture was diluted in 1×TE and *E. coli* K12 strain RR1 was transformed as described previously. Ampicillin-resistant colonies were picked and plasmid DNA purified by the rapid screening procedure described previously. The resulting plasmids, lacking the 0.4 Kb IBRV BglII to SstI fragment, were about 0.4 Kb smaller than pLATK dl NdeI, and were screened for the presence of SstI and BglII sites. The SstI site was preserved; however, the BglII site was unexpectedly lost. A representative plasmid was analyzed to confirm that the NG linker was present by hybridizing a $^{32}P$-labeled NG linker probe to plasmid DNA, as described in detail below. Working preparations of the plasmid, designated pLATK dl NdeI dl BglII/NG/SstI (see FIG. 3), were then prepared, as described previously.

I. Exonuclease Treatment of a pLATK dl NdeI Derivative to Remove Some of the Nucleotide Sequences 5' to the Coding Region of the tk Gene To delineate the approximate 5' boundaries of a functional IBRV tk gene, a series of plasmids were constructed with nucleotide deletions extending from the ClaI site of pLATK dl NdeI downstream to a point between the PvuII and BamHI cleavage sites (see FIG. 3, 0 to 1.6 map units). The exonuclease III digestion procedure of S. Henikoff (see: Henikoff, S., *Gene,* 28:351–359 (1984)) was followed.

A linker containing a KpnI cleavage site and EcoRI and ClaI cohesive ends was synthesized with the automated DNA synthesizer described above. The linker was obtained by first making a 15-mer nucleotide sequence (5'-AATTCGGTACCTCAT-3') and a 13-mer nucleotide sequence (5'-CGATGAGGTACCG-3'). These oligonucleotides contain 11 complementary base pairs. The complementary oligonucleotides were annealed to give a double-standard DNA fragment with a 5'-EcoRI 4 nucleotides, a 3'-ClaI cohesive end of 2 nucleotides, and a KpnI cleavage site in the double-stranded region.

To insert this linker between the EcoRI and ClaI sites of pLATK dl NdeI, the plasmid was digested with ClaI, and then with EcoRI, and the linearized plasmid was then ligated to the EcoRI-KpnI-ClaI linker by incubating with phage T4 DNA ligase overnight at 4° C. The modified pLATK dl NdeI plasmid was designated pLATK dl NdeI(Eco-Kpn-Cla).

The insertion of a unique KpnI site in pLATK dl NdeI(Eco-Kpn-Cla) was critical for the subsequent exonuclease III deletion procedure.

$$KpnI\begin{pmatrix}5'\text{-}GGTAC\downarrow C\text{-}3'\\ 3'\text{-}C\uparrow CATGG\text{-}5'\end{pmatrix}$$

digestion produces a 3' overhanging single-stranded end, which is resistant to exonuclease III digestion. However, after ClaI cleavage, the newly created ClaI end is susceptible to processive exonuclease III digestion. Thus, after KpnI and ClaI digestion, exonuclease III treatment of pLATK dl NdeI(Eco-Kpn-Cla) digests sequences clockwise, but the sequences counterclockwise on the plasmid are not digested.

The exonuclease III digestion of plasmid pLATK dl Nde(Eco-Kpn-Cla) to obtain deletion plasmids was carried out as follows:

5.0 μg of pLATK dl Nde(Eco-Kpn-Cla) in 100 μl of ClaI cutting buffer was digested with 20 units of ClaI (New England BioLabs, Inc.) at 37° C. for 2 hr. The reaction was stopped by addition of CDTA to 20 mM and sodium acetate was added to 0.1M followed by heating at 65° C. for 30 min. The DNA was ethanol precipitated and collected by centrifugation as described above.

The ClaI cleaved plasmid was redissolved in 100 μl of a KpnI cutting buffer, then digested by the addition of 20 units of KpnI (New England BioLabs, Inc.) for 2 hr at 37° C. The reaction was terminated, and the DNA precipitated with ethanol and collected as described above.

The ClaI and KpnI cleaved plasmid was redissolved in 66 mM Tris-HCl, pH 8.0, 0.6 mM $MgCl_2$ at a concentration of 100 μg/ml followed by the addition of 1/10 volume of exonuclease III (Bethesda Research Laboratories, Inc.; 65,000 units/ml) and incubated at 37° C. 5.0 μl aliquots were removed at 30 sec intervals and added to 15 μl of a solution comprising 0.2M NaCl, 5.0 mM EDTA, pH 8.0, and mixed. After heat inactivation of the exonuclease III activity at 70° C. for 10 min, 60 μl of ethanol was added and the DNA was precipitated overnight at −20° C. and collected by centrifugation.

The exonuclease III digested fractions were redissolved in 50 μl of a buffer comprising 0.25M NaCl, 30 mM potassium acetate (pH 4.6), 1.0 mM $ZnSO_4$, 5% (v/v) glycerol, and then digested with 6.8 units of Sl nuclease (Boehringer-Mannheim) at room temperature for 30 min. The reaction was stopped by the addition of 6.0 μl of 0.5M Tris-HCl (pH 8.0), 0.125M EDTA. The reaction mixture was extracted with phenol, and then chloroform, and next, the DNA was precipitated with two volumes of ethanol and collected by centrifugation.

For each of the samples obtained by sequential digestion, the ends were made flush with Klenow's enzyme. Specifically, the DNA was redissolved in 1×buffer comprising 6.0 mM Tris, pH 7.5, 6.0 mM $MgCl_2$, 1.0 mM dithiothreitol, 50 mM NaCl, and digested with 10 units/ml *E. coli* DNA polymerase, Klenow fragment (Bethesda Research Laboratories, Inc.) for 2 min at 37° C. Then, all four deoxynucleoside triphosphates were added to 0.1 mM and incubation was continued for an additional 2 min, followed by heating at 70° C. for 5 min, and ethanol precipitation and collection of the DNA as described above.

Each of the plasmids was recircularized by self-ligation in ligation buffer containing 1000 units of T4 DNA ligase overnight at 4° C. The reactions were terminated by adding EDTA to 20 mM and heating at 65° C. for 10 min.

The DNA ligation mixtures were diluted in 1×TE and used to transform *E. coli* K12 RR1 as described previously. The resulting transformants were screened by the rapid screening procedure described above and analyzed by agarose gel electrophoresis as described above. Plasmids which had retained progressive deletions were selected, and large-scale plasmid DNA preparations made as described previously.

Two of the plasmids, designated pLATK dl NdeI-(Exo36) and pLATK dl NdeI(Exo46), were later used for the construction of the phage pSP65 derivatives. These derivatives were transcribed and translated in vitro to give 37,000 dalton polypeptides. These studies, to be described in detail below, demonstrated that the translational start signal of the IBRV tk gene and the reticulocyte ribosomal binding sites were just downstream (3') to the site, labeled "36" of the nucleotide sequence shown in FIG. 4.

EXAMPLE 2

Nucleotide Sequence of the IBRV tk Gene

Fragments of the IBRV nucleotide sequence of plasmid pLATK dl NdeI (see FIG. 3) were subcloned in the double-stranded, replicative form (RF) of phage M13mp18 and M13mp19 (see: Hu, N. T. and Messing J., *Gene* 17:271–272 (1982) and Messing, J. and Vieira, J., *Gene* 19:269–276 (1982)). The use of these two phases permitted the cloning of small overlapping DNA fragments in two orientations. Then, replication of the recombinant phage M13 derivatives in *E. coli* K12 JM103 bacteria (New England BioLabs, Inc.) resulted in the synthesis of single-stranded phage DNA which could be used for sequencing reactions.

Sequencing reactions were carried out by the conventional dideoxynucleotide chain termination method (see: Sanger, F., Coulson, A. R., Barrell, B. G., Smith, A. J. H., and Roe, B. A., *J. Mol. Biol.* 143:161–178 (1980); Sanger, F., Nicklen, S., and Goulsen, A. R., *Proc. Nat. Acad. Sci.* USA 74:5436–5467 (1977)). The reaction mixture contained a single-stranded phage M13mp18 or M13mp19 subclone of IBRV DNA as template, either an M13 pentadecamer primer (New England BioLabs, Inc.) or synthetic oligonucleotide primer sequences of IBRV DNA made with the automated DNA synthesizer-Microsyn 1440 (Systec, Inc.) to initiate DNA synthesis on each of the templates, ($\alpha$-$^{32}$P)-dTTP as the labeled substrate, $Mg^{++}$, the appropriate unlabeled deoxyribonucleoside triphosphates and dideoxyribonucleoside triphosphates, and *E. coli* DNA polymerase, Klenow fragment (Bethesda Research Laboratories). After incubating the reaction mixture for 15 min at 38° C., a chase solution containing non-radioactive deoxyribonucleoside triphosphates was added. The reaction was terminated after 10 min at 38° C. by adding 10 $\mu$l of a 12.5 mM EDTA solution containing 0.3M sodium acetate and 200 $\mu$g of yeast tRNA (Sigma Chemical Co.). The reaction products were precipitated with ethanol, dissolved in 10 $\mu$l of a solution comprising 90% (v/v) formamide, 30 mM NaOH, 10 mM EDTA, 0.3% (w/v) bromphenol blue, and 0.3% (w/v) xylene cyanol, heated for 1 min at 90° C., and loaded into 8% (w/v) sequencing gels comprising 7.6% (w/v) acrylamide, 0.4% (w/v) bisacrylamide, 0.003% (v/v) TEMED, 0.007% (w/v) ammonium persulfate, and 17% (v/v) formamide.

The nucleotide sequence, designated LATK16, of a 2814 bp XhoI to SalI fragment containing the IBRV tk gene is shown in FIG. 4. Although the nucleotide sequence shown in FIG. 4 was obtained by sequencing the tk gene of IBRV(Los Angeles), due to the high evolutionary conservatism of the IBRV tk gene, other tk+ IBRV strains, as exemplified above, would be expected to have tk genes with substantially similar nucleotide sequences, and, thus, as discussed below, the nucleotide sequence in FIG. 4 can be employed to construct additional tk− IBRV deletion mutants employing tk+ IBRV strains other than IBRV(Los Angeles) as the starting material.

In FIG. 4, the XhoI site (CTCGAG) at the start of the sequence corresponds to the pLATK dl NdeI XhoI site at 0.5 map units (see FIG. 3). The sequence then extends clockwise from the XhoI site to the SalI site (GTCGAC) of pLATK dl NdeI at 3.4 map units. TA-rich sequences, which might serve as parts of transcriptional control signals, are underlined at nucleotides 1127 and 1229. A putative "CAAT" box, which, likewise, might be part of a transcriptional control signal, is also underlined. A putative translational start signal, i.e., ATG, for the IBRV TK polypeptide is at nucleotide 1292. This ATG codon is the first ATG codon to follow the TTAAAAA sequence at nucleotide 1127, consistent with the hypothesis (see: Kozak, M. *Nucl. Acids Res.,* 9:5233–5252 (1981)) that eukaryotic ribosomes usually initiate protein synthesis at the AUG closest to the 5′ end of an RNA. Kozak has also observed that eukaryotic mRNAs almost always have a purine at position −3 from the ATG or a G at +3, or both. It may be seen that the sequence GCCATGG (nucleotides 1289–1295) conform to this rule. A putative translational stop signal, i.e., TAA, for the IBRV tk gene is at nucleotide 2366.

The nucleotide sequence of FIG. 4 contains one open reading frame which can be translated to a 358 amino acid polypeptide with a molecular weight of 36,903. The predicted amino acid sequence of this polypeptide is shown in the three-letter notation of the IUPAC-IUB Commission on Biochemical Nomenclature (see: *Europ. J. Biochem.* 5:151–153 (1968)). The size of the predicted IBRV TK polypeptide is similar to that of the HSV-1, HSV-2, and *Herpesvirus tamarinus* TK polypeptides (see: Otsuka H. and Kit, S., *Virol.* 135:316–330 (1984) and Kit., S., Kit, M., Qavi, H., Trkula, D., and Otsuka, H., *Biochim. Biophys. Acta* 741:158–170 (1983)). Furthermore, amino acid residues 10 to 27 of the predicted IBRV TK polypeptide are homologous to amino acid residues 49 to 66 of the HSV-1 and HSV-2 TK polypeptides and amino acid residues 10 to 27 of the *Herpesvirus tamarinus* TK polypeptide, which appear to represent a conserved ATP-binding pocket of the TK enzyme. Finally, in vitro translation products of the transcripts obtained from this sequence exhibit a molecular weight of about 37,000, consistent with the predicted size of the IBRV TK polypeptide (see below for details).

The other two reading frames of the IBRV DNA strand shown in FIG. 4 as well as the three reading frames of the complementary strand contain many translational stop signals and cannot be translated into polypeptides of 35,000 to 40,000 molecular weight.

Restriction nuclease sites for more than 75 different restriction nucleases are predicted from the nucleotide sequence shown in FIG. 4. Some of the common restriction nucleases with only one to three cleavage sites in the sequence are shown in Table 2 below.

TABLE 2

Restriction Nuclease Cleavage Sites Predicted from the Nucleotide Sequence of the IBRV tk Gene

| Restriction endonuclease | Location of first nucleotide in sequence (Nucleotide No.) |
|---|---|
| ApaI | 884, 2350 |
| BamHI | 1248, 1473, 2438 |
| BglII | 1759 |
| MluI | 490, 2220 |
| PvuI | 700, 792, 2408 |
| PvuII | 928 |
| SacI (SstI) | 2102 |
| SalI | 170, 2808 |
| SphI | 831 |
| XhoI | 1, 2183 |

It should be noted that unique BglII and SacI (SstI) cleavage sites occur at nucleotides 1759 and 2102, respectively. The sequences bracketed by these cleavage sites were deleted from plasmid pLATK dl NdeI in the isolation of plasmid pLATK dl NdeI dl BglII/NG/SstI (see FIG. 4). This deletion eliminates about 113 amino acid residues from the coding sequence of the IBRV tk gene. Furthermore, the ligation of the NG linker at the BglII/SstI sites of pLATK dl NdeI dl BglII/NG/SstI would also be expected to change the translational reading frame and to introduce translational stop signals, i.e., TGA and TAA, in all three reading frames, thereby aborting translation of the sequence beyond the BglII cleavage site.

The predictions of restriction nuclease cleavage sites are consistent with the restriction map of pLATK dl NdeI (see FIG. 3) and provide precise data on sites that might be used for engineering other deletion mutations in plasmid pLATK dl NdeI, and thus, other tk− deletion mutants of the present invention.

It should also be noted that deletions can be made in plasmid pLATK dl NdeI by modifications of the procedures described in detail herein. For example, it is not essential that the NG linker be ligated to the BglII/SstI termini after endonuclease cleavage of plasmid pLATK dl NdeI. That is, the cleaved plasmid could have been treated with exonucleases to create "blunt ends", or to widen the deletion gap and then ligated with phage T4 DNA ligase in the absence of a nucleotide linker.

EXAMPLE 3

In Vitro Transcription and Translation of the IBRV tk Gene

The 3 Kbp vectors, pSP64 and pSP65, are well known and have been constructed for convenient use as standard subcloning vectors and as templates for highly efficient in vitro transcription (see: Melton, D. A. et al, *Nucl. Acids Res.* 12:7035–7056 (1984) and Promega Biotech 1985/1986 catalogue and applications guide). These vectors contain a phage SP6 promoter cloned into a pUC12-derived plasmid, immediately upstream from a phage M13 polylinker, which makes possible a broad range of cloning strategies. There are 11 restriction enzyme sites unique to the polylinker and the polylinker orientation is inverted in the two vectors.

To learn whether the IBRV DNA sequence tentatively identified as the tk gene could be transcribed and translated in vitro to a 37,000 dalton polypeptide, as predicted (see FIG. 4), IBRV DNA sequences were transferred from plasmid pLATK dl NdeI(Exo36) and pLATK dl NdeI(Exo46) to plasmid pSP65, as described below. The former plasmid contained the pLATK16 sequence starting at nucleotide 1090 and the latter starting at nucleotide 1130 (see FIG. 4).

1 μg of pSP65 DNA was mixed with 1.0 μg of pLATK dl NdeI(Exo36) or pLATK dl NdeI(Exo46) and cleaved first with EcoRI in EcoRI cutting buffer described above and then with PstI in PstI cutting buffer comprising 100 mM NaCl, 10 mM Tris-HCl, pH 7.4, 10 mM $MgCl_2$ and 100 μg/ml BSA, in a final volume of 20 μl. The reaction was stopped by adding EDTA to a final concentration of 20 mM and heating at 65° C. for 20 min. Then, 20 μl of phenol:chloroform (1 vol:1 vol) was added, the mixture was shaken, and then centrifuged in the Eppendorf centrifuge. The aqueous (upper) phase was transferred to another tube, and 2 volumes of ethanol were added to precipitate the cleaved DNAs. The DNA precipitate was washed with 70% (v/v) ethanol, dried in vacuum, redissolved in 40 μl of ligation buffer containing 400 units of phage T4 DNA ligase (New England BioLabs, Inc.), and incubated overnight at 4° C. The reaction was terminated by adding 160 μl of TE buffer and heated at 65° C. for 10 min.

$CaCl_2$-activated *E. coli* K12 RRl cells were next transformed with the ligated DNAs and ampicillin-resistant, tetracycline-sensitive colonies were screened for the presence of a pSP65 derivative containing a 2 Kbp EcoRI/PstI insert. The structures of the plasmids, designated pSP65(Exo36) and pSP65(Exo46) were confirmed by restriction endonuclease mapping with EcoRI, BamHI, BglII, SacI, XhoI, SalI, and PstI.

To prepare transcripts of pSP65(Exo36) and pSP65(Exo46), these plasmids were linearized by digesting them with SalI and then resuspended at a concentration of 1.0 μg/ml in distilled water that had previously been treated with 0.01% (v/v) diethylpyrocarbonate (hereinafter "DEPC") to inactivate any RNase activity. Then, the following procedure was used.

(a) In vitro transcription:

To a sterile DEPC-treated tube was added:

(1) 19 μl water (sterile distilled water, DEPC-treated)

(2) 10 μl 5× transcription buffer (200 mM Tris-HCl, pH 7.5 (measured at 37° C.), 30 mM $MgCl_2$, 10 mM spermidine, 50 mM NaCl)

(3) 5.0 μl of 0.1M dithiothreitol (4) 2.0 μl RNAsin (40 units/μl ) (Promega)

(5) 10 μl of 5× rNTPs (10 mM GTP, 10 mM ATP, 10 mM CTP, 10 mM UTP) (Promega)

(6) 2.0 μl DNA (1.0 μg/μl linear)

(7) 2.0 μl SP6 RNA polymerase (Bethesda Research Laboratories; 5–10 units/μg DNA)

The mixture was incubated at 40° C. for 1 hr and 1.0 μl of 100 μg (200 units/100 μl DNase I) (Cooper Biomedical; DPRF grade; 11,290 units/5.6 ml in 50% (v/v) glycerol; stored at −20° C.) was added, followed by 1.0 μl of RNAsin (40 units/μl (Promega)).

The mixture was again incubated at 37° C. for 10 min and then extracted with an equal volume of phenol:-chloroform (1 vol:1 vol) once. 1/10 the volume of 1.0M potassium acetate, pH 7.0, and 2.2 volumes of ethanol were added. The suspension was then incubated at −20° C. for at least 2 hr.

(b) mRNA capping:

The ethanol precipitated RNA was centrifuged in an Eppendorf centrifuge for 5 min and the supernatant removed by aspiration. The RNA pellet was dried under vacuum and resuspended in 17.8 μl of sterile DEPC-treated water.

The following substances were next added in the order given:

(1) 6.0 μl of 5× capping buffer, comprising: 250 mM Tris-HCL pH 7.9; 6.25 mM $MgCl_2$; 30 mM KCl; 12.5 mM dithiothreitol; 500 μg/ml BSA (2) 1.0 μl RNAsin (40 units/μl (Promega))

(3) 3.0 μl of 1.0 mM S-adenosyl-methionine (Sigma Chemical Co.)

(4) 1.2 μl of 1.0 mM GTP (Promega)

(5) 1.0 μl of guanylyl transferase (Bethesda Research Laboratories)

The reaction mixture, 30 μl, was incubated at 37° C. for 45 min, extracted with phenol:chloroform (1 vol:1 vol), and then the capped RNA transcript was precipitated by adding 1/10 volume of 1.0M potassium acetate, pH 7.0, and 2 volumes of ethanol.

(c) Translation of capped mRNA:

Translation of the capped RNA transcript was carried out with the nuclease-treated rabbit reticulocyte lysate (Promega) as follows:

(1) The RNA was sedimented by centrifuging for 5 min in the Eppendorf centrifuge and the supernatant was removed by aspiration.

(2) The pellet was washed in ethanol and incubated at −20° C. for 30 min. The centrifugation step was repeated and the pellet was dried in vacuum.

(3) To the RNA pellet was added in a total volume of 50 μl, ice cold solutions of:

(a) 8.0 μl water (sterile; treated with DEPC)

(b) 1.0 μl RNAsin (40 units/μl; Promega)

(c) 5.0 μl $^{35}$S-methionine (New England Nuclear; 10 μCi/μl)

(d) 1.0 μl of 1.0 mM amino acid mixture (without methionine) (Promega)

(e) 35 μl reticulocyte lysate (Promega)

The reaction mixture was incubated at 30° C. for 1.5 to 2 hrs.

At the end of the incubation period, the translation products were denatured for polyacrylamide gel electrophoresis.

(d) Denaturing procedure:

Water was added to the reaction volume (50 μl) to give a final volume of 200 μl. Then 100 μl of buffer D comprising 0.0625M Tris, pH 6.8, 0.3% (w/v) sodium dodecyl sulfate, 5.0% (v/v) mercaptoethanol, 10% (v/v) glycerol, and 0.001% (w/v) bromphenol blue, was added, the mixture was boiled for 2 min, and stored at −80° C. until used.

(e) Polyacrylamide gel electrophoresis of protein translation products:

5×electrophoresis buffer consisted of:

(1) 144 g glycine (Calbiochem)

(2) 30 g Trizma (Sigma Chemical Co.)

(3) 5.0 g sodium dodecyl sulfate (Bethesda Research Laboratories)

Polyacrylamide gels were made as follows: The 3.0% stacking gel consisted of:

(1) 3.17 ml $H_2O$ (2) 1.25 ml upper Tris buffer (4×0.5M Tris-HCl, pH 6.8, 0.4% (w/v) sodium dodecyl sulfate)

(3) 0.5 ml acrylamide:bisacrylamide (30:0.8 (w/w))

(4) 75 μl 2.0% (w/v) ammonium persulfate (5) 5.0 μl TEMED (Sigma Chemical Co.)

The 10% running gel consisted of:

(1) 12 ml $H_2O$ (2) 7.5 ml lower Tris (4×1.5M Tris-HCl, pH 8.8, +0.4% (w/v) sodium dodecyl sulfate)

(3) 10 ml acrylamide:bisacrylamide (30:0.8 (w/w))

(4) 0.6 ml 2.0% (w/v) ammonium persulfate (5) 15 μl TEMED (6) 0.5 ml 50% (v/v) glycerol 75 μl aliquots of the translation products were applied to 1.5 mm thick Laemmli gels and electrophoresed at 40 volts, constant voltage, for 16 hr at room temperature. The gels were fixed and stained for 30 min at room temperature with a solution comprising 50% (v/v) methanol, 10% (v/v) acetic acid, and 0.015% (w/v) coomassie blue, then destained for 2 hr at room temperature with a solution comprising of 10% (v/v) acetic acid and 10% (v/v) methanol. The gel was next dried and subjected to direct autoradiography with Fuji X-ray film at −70° C. for 1 day.

When the pSP65(Exo46) and the pSP65(Exo36) plasmids were transcribed and translated as described above, a radioactive band with a molecular weight of about 37,000 daltons was detected. Bands were not detected when the RNA transcript was omitted from the translation reaction. These results demonstrate that the nucleotide sequence extending downstream from the point marked "46" (nucleotide 1129 of FIG. 4) to the PstI site of pLATK dl NdeI (FIG. 3, 3.6 map units) contains an open reading frame translatable to a polypeptide with a molecular weight of about 37,000.

EXAMPLE 4

Construction of tk⁻ Deletion IBRV Mutant

A. Recombination of Hybrid Plasmid and tk⁻ IBRV DNA

It was shown above that homologous recombination between intact DNA of a $tk^-$ IBRV strain, i.e., IBRV(B8-D53), and a hybrid plasmid containing the coding region of the IBRV tk gene, i.e., pLAH-A, resulted in the rescue of a functional tk gene in the recombinant virus, designated IBRV (RTK-1B).

In order to obtain, by homologous recombination, an IBRV deletion mutant in the tk gene, it was necessary to start with the intact DNA of a $tk^+$ IBRV and a hybrid plasmid containing a deletion in the coding region of the tk gene. The progeny virus obtained following this type of cross mainly comprise parental $tk^+$ IBRV. Thus, in order to enrich for the $tk^-$ IBRV recombinants in the harvests, selective media containing BrdUrd was employed, since BrdUrd inhibits $tk^+$ IBRV replication and favors the outgrowth of $tk^-$ IBRV.

The hybrid plasmid chosen for the construction of a $tk^-$ deletion mutant of IBRV was pLATK dl NdeI dl BglII/NG/SstI. However, other hybrid plasmids containing larger or smaller flanking sequences adjacent to the coding sequence of the IBRV tk gene (see FIG. 4) or larger or smaller deletions in other portions of the tk gene, could be employed to create "deletion" mutations, without departing from the scope and spirit of this invention.

The 3.7 Kbp ClaI to NdeI fragment from pLATK dl NdeI dl BglII/NG/SstI was excised from the hybrid plasmid by adding 10 μg of pLATK dl NdeI dl BglII/NG/SstI to ClaI cutting buffer containing 20 units of ClaI and digesting at 37° C. for 3 hr, followed by the addition of 100 units of NdeI in an equal volume of NdeI cutting buffer, augmented with an additional 100 mM NaCl, and digested at 37° C. for 3 hr. The reaction was terminated by adding an equal volume of 90% (v/v) phenol, mixed, and centrifuged for phase separation. After dialysis of the aqueous phase against 0.1×TE, the DNA was adjusted to 10 μg/ml and filter sterilized.

The $tk^+$ IBRV DNA chosen for the recombination step was IBRV(RTK-1B). Since IBRV(RTK-1B) was derived from IBRV(B8-D53), a vaccine strain attenuated through multiple mutations induced by mutagens, the IBRV(RTK-1B) was the preferred virus to other $tk^+$ IBRV field strains for the construction of the deletion mutant. However, as described above, other strains would be equally suitable without departing from the scope and spirit of this invention.

The construction of the recombinant $tk^-$ deletion mutant of IBRV(RTK-1B) was carried out as follows: RAB-9 cells were seeded in 60 mm Petri dishes ($0.2\times10^6$ cells per dish) and incubated at 37° C. for 48 hr. Then, the following sterile solutions were added to a test tube in sequential order:

(1) 0.02 ml of a 50 μg/ml solution of IBRV(RTK-1B) DNA in TE buffer;

(2) 0.2 ml of a 10 μg/ml solution of hybrid plasmid pLATK dl NdeI dl BglII/NG/SstI cleaved with ClaI and NdeI;

(3) 0.65 ml of water;

(4) 1.0 ml of 20 μg/ml solution of salmon sperm DNA in 2×Hepes buffer solution comprising 16 g/l NaCl, 0.74 g/l KCl, 0.25 g/l $Na_2HPO_4.2H_2O$, 2.0 g/l glucose, 10 g/l Hepes, pH 7.05 (hereinafter "2×Hepes buffer solution");

(5) 0.13 ml of 2.0M $CaCl_2$

The resulting solution was mixed by inversion and kept at room temperature for 30 min while a DNA-calcium phosphate precipitate formed. Then, 0.5 ml of the suspension containing a calcium phosphate precipitate of DNA was added directly to 5.0 ml of growth medium and plated on RAB-9 cells which had been seeded in 60 mm Petri dishes 48 hr earlier. The cells were incubated at 37° C. for 5 hr. Then the media was aspirated, and the monolayer rinsed with 5.0 ml of fresh growth media, followed by the addition of 1.0 ml of a solution of 1×Hepes buffer solution plus 15% (v/v) glycerol. After a 3 min incubation at room temperature, the solution was aspirated, the monolayer rinsed with media again, and fresh growth media added. The culture were incubated at 34.5° C. for 3 days until extensive cytopathic effects occurred. Virus harvests were made as described above and stored at −80° C. The virus harvest was then titrated in RAB-9 cells under agar overlay.

The virus harvest from the co-transfection was thawed, sonicated, and diluted in growth media supplemented with 50 μg/ml BrdUrd. In order to enrich for tk− IBRV deletion mutants, the harvested virus was diluted to give an input multiplicity of 0.1 PFU/cell and passaged in confluent monolayer cultures of RAB(BU) cells in 8-ounce prescription bottles in growth medium supplemented with 50 μg/ml BrdUrd. After a 1 hr absorbtion at 37° C., the infected monolayer cultures were washed three times with GKN. Then, growth medium containing 50 μg/ml BrdUrd was added, incubation was continued at 34.5° C. for 48 hr, and virus harvests were made.

The harvest of the first selection step was titrated, and a second selection step carried out as before. The harvest of the second selection step was titrated in RAB-9 cells, candidate tk− deletion mutants of IBRV were picked at random from plaques, and virus pools were prepared. In this manner, 96 tk− IBRV deletion mutant candidates were obtained.

B. Preparation of Probes for Molecular Hybridization

To verify that deletions existed in the tk gene of the tk− IBRV deletion mutant candidates, along with the presence of the NG linker, molecular hybridization experiments with $^{32}$P-labeled probes were carried out:

(1) Preparation of BglII/SacI(SstI) probe:

This probe was made by nick translation of the RF form of phage M13mp19(BglII/SacI), which was made by inserting the BglII to SacI(SstI) nucleotide sequence of pLATK dl NdeI into phage M13mp19 (see: Yanisch-Perron, C., Vieira, J., and Messing, J., *Gene* 33:103–119 (1985)) as described in detail below. (Also see FIG. 4, LATK16 sequence from nucleotide 1759–2102).

M13mp19(BglII/SacI) was constructed as follows. First, a mixture of the RF form of phage M13mp19 and pLATK dl NdeI was cleaved with BamHI and SacI. The reaction products were ligated with phage T4 DNA ligase, used to transform $CaCl_2$-activated *E. coli* JM105 bacteria, and screened for transformants containing a 629 bp BamHI-BglII-SacI insert (see FIG. 4, nucleotides 1473 to 2102 of LATK16). The M13mp19 recombinant obtained in this manner was designated phage 19-301.

The RF form of phage 19-301 was prepared and cleaved successively with BamHI and BglII, ligated with phage T4 DNA ligase, and used to transform $CaCl_2$-activated *E. coli* JM105 bacteria. Since BglII and BamHI cleaved DNAs have the same cohesive ends, most of the recombinant phage obtained from this transformation lacked the 286 bp BamHI to BglII fragment of phage 19-301 and LATK16 sequence from nucleotides 1473 to 1759), but retained the LATK16 sequence from nucleotides 1759 to 2102 (see FIG. 4). The RF phage DNA was prepared from a candidate recombinant phage; the structure of the phage, designated M13mp19(BglII/SacI), was then confirmed by restriction nuclease mapping. $^{32}$P-labeled probes were prepared by nick translation of the RF form of M13mp19(BglII/Sac), as described below. Alternatively, the RF form of M13mp19(BglII/SacI) was first cleaved with SacI and PstI (PstI is a cloning site on the polylinker cloning region of M13mp19 upstream from the BglII/BamHI junction of the IBRV/M13mp19 insert (see New England BioLabs' 1985/1986 catalogue, p. 47), and the SacI to PstI fragment was purified by centrifugation in a 10–40% (w/v) sucrose gradient at 39,000 rpm for 20 hr and nick-translated.

To 25 μl of reaction mixture containing 6.0 μmol PBS, pH 7.4; 1.8 nmol dATP; 1.8 nmol dGTP; 0.1 mCi ($\alpha$-$^{32}$P)dTTP (400 Ci/mmole); 0.1 mCi ($\alpha$-$^{32}$P)dCTP (400 Ci/mmole) (Amersham Corporation), about 1.0 μg plasmid DNA was added. Then, 1.33 ng in 1.0 μl of DNase I (Worthington Biochemical Corporation) was added and the reaction mixture was allowed to stand for 1 min at room temperature. Next, the reaction mixture was incubated at 14° C. with 5.0 units in 1.0 μl of *E. coli* DNA polymerase I (Boehringer-Mannheim Biochemicals). When the specific activity became higher than $2\times10^8$ cpm/μg DNA, i.e., about 3 hr, the reaction was terminated by adding 10 μl of 0.25M EDTA (pH 7.4) and heating at 68° C. for 10 min. Then, as carrier, 50 μl of a solution comprising 5.0 mg/ml sonicated salmon sperm DNA in TE buffer, was added to the mixture and the nick-translated DNA was purified by Sephadex G50 (fine) column chromatography using 10 mM NaCl, 10 mM Tris-HCl, pH 7.5, 2.0 mM EDTA as the elution buffer.

The resulting 32P-labeled, nick-translated DNA was used as a probe in DNA-DNA hybridization experiments after boiling in a water bath for 20 min, and quickly cooling on ice to form single-stranded DNA (see: Rigby, P. W. J., Dieckmann, M., Rhodes, G., and Berg, P., *J. Mol. Biol.* 113:237–251 (1977)).

(2) pLATK dl NdeI Probe:

This probe was made by nick translation of plasmid pLATK dl NdeI (see FIG. 3).

(3) NG Probe Linker:

Synthesis of the NG linker has been described above. To prepare a probe, the NG linker was labeled with $^{32}$P as follows:

50 picomoles of NG linker was added to a reaction mixture comprising 150 μCi$\gamma$-$^{32}$P ATP, 70 mM Tris-HCl (pH 7.6), 10 mM $MgCl_2$, 5.0 mM dithiothreitol, and 5 units of T4 polynucleotide kinase (New England BioLabs, Inc.). The mixture was incubated for 1 hr at 37° C. and the reaction was terminated by adding EDTA to 20 mM, followed by purification of the labeled NG linker by gel filtration on gel P4 (Bio-Rad, Inc.) to remove the unreacted$\gamma$-$^{32}$P ATP. The elution buffer was the same as that used for Sephadex G-50 chromatography discussed above. The probe was not heat-treated before use, since it was already single-stranded.

C. Identification of Recombinant tk− IBRV Deletion Mutant of IBRV(RTK-1B) By Molecular Hybridization Viral DNAs prepared from the candidate recombinants described previously were analyzed by the dot blot method (see: Brandsma, J. and Miller, G., *Proc.*

Nat. Acad. Sci. USA 77:6851–6855 (1980)) to identify viruses that lacked the 0.4 Kbp BglII to SstI IBRV tk gene fragment. Specifically, 24-well multiwell tissue culture trays containing confluent monolayers of RAB-9 cells were infected with 0.05 ml of undiluted candidate virus and incubated at 34.5° C. for 8 hr. The virus inoculum was aspirated, the wells rinsed with 1.0 ml of GKN, and 0.2 ml of 0.5N NaOH was added to each well to lyse the cells and release the DNA. After storage at room temperature overnight, 0.3 ml of 1.0M Tris-HCl (pH 7.5) and 0.5 ml of 20×SSC buffer comprising 3.0M NaCl, 0.3M sodium citrate, pH 7.0 (hereinafter "20×SSC") were added per well. For dot blot analysis, nitrocellulose filters in a 96-well Schleicher and Schuell filtration apparatus was used. The filters were washed with water and with 1×SSC prior to the addition of the DNA samples. To bake the DNA samples to the filters, the nitrocellulose filters were dried, heated overnight at 60° C. in a vacuum desiccator, and then heated for 2 hr at 80° C. The filter was placed in a plastic sealable pouch containing 50 ml of 3×SSC, 0.02% (w/v) Ficoll, 0.02% (w/v) BSA, 0.02% (w/v) polyvinylpyrrollidone, 50 μg/ml of boiled and alkali-denatured salmon sperm DNA (hereafter called "modified Denhardt's solution"), 10 μg/ml poly(A) and incubated overnight at 60° C. with shaking. Alkaline salmon sperm DNA was added from a stock solution of about 5.0 mg/ml prepared by dissolving 50 mg of salmon sperm DNA in 10 ml of 0.2N NaOH, heating at 100° C. for 20 min to denature and shearing the DNA to about 0.4 kb segments, and then neutralizing with 0.2 ml of 10N HCl.

The modified Denhardt's solution was then replaced with 50 ml of hybridization buffer comprising 50% (v/v) formamide, 0.6M NaCl, 0.2M Tris-HCl, pH 8.0, 0.02M EDTA, 0.1% (w/v) sodium dodecylsulfate, 50 μg/ml alkali-denatured salmon sperm DNA, and 10 μg/ml poly(A) (hereafter called "hybridization buffer"). Next, air bubbles were squeezed out of the bag which was then sealed using an Oster Touch-a-Matic Bag Sealer and incubated at 37° C. for 1 hr on a shaker.

Thereafter, about 1.0 ml, containing about $10^7$ cpm and 50 ng, of single-stranded ($^{32}P$) nick-translated BglII/SacI probe, obtained as described above, was added to the bag with a 3.0 ml syringe by piercing the side of the bag at a corner. Next, the bag was resealed and incubated at 37° C. for up to 48 hr on a shaker to allow for hybridization.

After hybridization had been accomplished, the bag was cut and the solution was decanted. The filter was then carefully removed and placed into a tray containing about 100 ml of hybridization buffer containing 50 μg/ml denatured salmon sperm DNA for the first wash only, but no poly(A) in any wash. The filter was washed for 30 min at 37° C. five times with gentle shaking. Next, the filter was washed for 30 min at 37° C. with 0.3×SSC and then placed on filter paper to dry overnight at room temperature.

For autoradiography, the filter was replaced on a thin piece of cardboard covered with Saran-Wrap, and exposed to Fuji X-ray film with an intensifying screen for periods of 5 hr to 2 days a −70° C. About 35 out of the 96 candidate viruses did not hybridize to the BglII/SacI probe, indicating that these clones had a deletion in the BglII to SacI(SstI) sequence of the IBRV tk gene. Two clones were saved for further analysis and designated IBRV(NG) dl TK clone 1 and IBRV(NG) dl TK clone 5.

Viral DNA of high purity was prepared as described above. 0.5 μg of viral DNA from each of the candidate deletion mutants was cleaved with restriction nucleases, HindIII, BamHI, KpnI, and SalI, under conditions specified by New England BioLabs, and the fragments were separated by electrophoresis on 0.6% (w/v) agarose at 35 volts (constant voltage) for 16 hr at 4° C. The electrophoresis buffer was 0.04 M Trizma base, pH 8.1, 0.03M $NaH_2PO_4$, and 0.001M EDTA. Restriction nuclease fragments of the parental IBRV(RTK-1B) and marker fragments obtained by HindIII digestion of phage lambda DNA and HaeIII digestion of phage ΦX174 RF DNA were also electrophoresed. The gels were stained with ethidium bromide and photographed as described above to reveal the DNA fragments.

The results demonstrated that the 6.7 Kbp KpnI and the 2.8 Kbp SalI fragments of IBRV(RTK-1B) (see FIG. 2, plasmid pLAK map units 1.6 to 8.3, and FIG. 3, plasmid pLATK dl NdeI map units 0.6 to 3.4) were specifically altered, and that new, more rapidly migrating (smaller) fragments were present in the deletion mutant samples. This is consistent with the deletion of the approximately 0.4 BglII/SacI sequence from the IBRV tk gene. As expected, no mobility shifts were apparent in the HindIII-A fragments of the deletion mutants because the small deletion was obscured by the large size (21.4 Kbp) of the HindIII-A fragment. Likewise, a 1.1 Kbp BamHI fragment (BamHI-J fragment) of IBRV(RTK-1B) (see FIG. 3, plasmid pLATK dl NdeI map units 2.0 to 3.1) was about 0.4 kb smaller in the deletion mutant DNA fragments than in the BamHI fragments of IBRV(RTK-1B).

After electrophoresis, the separated DNA restriction fragments in the agarose gel were transferred to nitrocellulose filters (Schleicher and Schuell) for molecular hybridization experiments in the following manner: The agarose gel was placed in a glass baking tray containing 1.0M KOH for 30 min at room temperature and, then, in a glass baking tray containing 1.0M Tris-HCl, pH 7.0 and 0.6M NaCl for 60 min at room temperature. The treated gel was then transferred to a blot apparatus (Bethesda Research Laboratories).

A nitrocellulose filter was prewetted in water for 10 min and then in 20×SSC for 5 min. Next, the filter was placed on the gel. Using 20×SSC as the transfer fluid, blotting was allowed to proceed for about 24 hr. The adherent gel was removed from the nitrocellulose filter, and the filter was rinsed with 6×SSC, dried at room temperature for several hours, and then in a vacuum desiccator overnight at 60° C. This was followed by 2 hr of baking at 80° C. The nitrocellulose filters were removed from the desiccator and placed in Dazey Seal-a-Meal cooking bags (see: Southern, E. M., *J. Mol. Biol.* 98:503–513 (1975)).

The filter was first pretreated overnight at 60° C. with 50 ml of modified Denhardt's solution and hybridization buffer at 37° C. as described previously.

The nitrocellulose filters from three separate gels were next hybridized to three separate $^{32}P$-labeled probes: (i) BglII/SstI probe; (ii) pLATK dl NdeI probe; and (iii) NG linker probe. The procedure for molecular hybridization of the probes to the nitrocellulose filters and the washing step were the same as described previously, except that in the case of the 32P-labeled NG linker probe, the hybridization reaction was carried out in 35% (v/v) formamide, 0.6M NaCl, 20 mM EDTA, 0.2M Tris, pH 8.0, 0.1% (w/w) sodium dodecylsulfate solution and the final wash was with 6×SSC.

The results demonstrated that the BglII/SstI probe hybridized specifically to a 21.4 kb HindIII fragment, a 1.1 kb BamHI fragment, a 6.7 kb KpnI fragment and a 2.8 kb SalI fragment of IBRV(RTK-1B) DNA but not to fragments of either HindIII-, BamHI-, KpnI- or SalI-cleaved IBRV(NG) dl TK clones 1 and 5 DNA.

In addition, the results demonstrated that the pLATK dl NdeI probe hybridized specifically to: (1) an approximately 21 kb HindIII fragment of IBRV(RTK-1B) DNA and to a 21 kb HindIII fragment of IBRV(NG) dl TK clones 1 and 5 DNA; (2) 17.3 kb, 15.7 kb and 1.1 kb BamHI fragments of IBRV(RTK-1B) DNA and to 17.3 kb, 15.7 kb and 0.7 kb BamHI fragments of IBRV(NG) dl TK clones 1 and 5 DNA; (3) a 6.7 kb KpnI fragment of IBRV(RTK-1B) DNA and to a 6.3 kb KpnI fragment of IBRV(NG) dl TK clones 1 and 5 DNA; and (4) 2.8 kb and 0.8 kb SalI fragments of IBRV(RTK-1B) DNA and to 2.4 kb and 0.8 kb SalI fragments of IBRV(NG) dl TK clones 1 and 5 DNA. The 1.1 kb BamHI, 6.7 kb KpnI and 2.8 kb SalI fragments of IBRV(RTK-1B) DNA, which contain the tk gene, were larger by 0.4 kb than the corresponding fragments of IBRV(NG) dl TK clones 1 and 5 DNA; i.e., the 0.7 kb BamHI, 6.3 kb KpnI and 2.4 kb SalI fragments. There was no apparent change in the about 21 kb HindIII fragment of IBRV(NG) dl TK clones 1 and 5 DNA because of the large size of the HindIII-A fragment relative to the size of the introduced deletion.

Further, the results demonstrated that the NG linker probe hybridized specifically to the about 21 kb HindIII, 0.7 kb BamHI, 6.3 kb KpnI and 2.4 kb SalI fragments of IBRV(NG) dl TK clones 1 and 5 DNA, but did not hybridize to the fragments of IBRV(RTK-1B) DNA.

These experiments conclusively demonstrate that IBRV(NG) dl TK clones 1 and 5 genomes had a BglII/SstI deletion of about 0.4 kb and an NG linker insertion in the IBRV tk gene. IBRV(NG) dl TK clone 1 has been deposited with the American Type Culture Collection under ATCC No. VR-2112.

EXAMPLE 5

TK Activity of IBRV Strains

To verify that deletion mutant IBRV(NG) dl TK clone 1 lacked the ability to induce functional TK activity, TK induction experiments were carried out. More specifically, subconfluent monolayer cultures of RAB(BU) cells were mock-infected or infected for 7 hr with the IBRV(Los Angeles) or the IBRV(NG) dl TK clone 1 strains. Cytosol fractions were prepared and assayed for TK activity (see: U.S. Pat. No. 4,514,497 and Kit, S. and Qavi, H., *Virol.* 130:381-389 (1983)). The results obtained are shown in Table 3 below.

TABLE 3

Cytosol Thymidine Kinase Activity of RAB(BU) Cells Infected for 7 Hr with tk+ IBRV and tk− IBRV Strains

| IBRV strain used to infect RAB(BU) cells | TK activity (picomoles dTMP formed in 10 min at 38° C. per μg protein) |
|---|---|
| Mock-infected RAB(BU) | 0.04 |
| IBRV(Los Angeles) | 1.74 |
| IBRV(NG) dl TK clone 1 | 0.03 |

Table 3 above demonstrates that: (i) RAB(BU) cells, i.e., tk− rabbit skin cells, have negligible TK activity; (ii) TK activity is acquired by RAB(BU) cells after infection by tk+ IBRV(Los Angeles), but not after infection by the tk− deletion mutant, IBRV(NG) dl TK clone 1. Thus, deletion of the BglII/SacI fragment from the IBRV tk gene results in total loss of TK-inducing activity.

EXAMPLE 6

Temperature Resistance of IBRV Strains

Replicate, subconfluent monolayer cultures of RAB-9 cells were infected with IBRV(NG) dl TK clone 1 at an input multiplicity of about 0.01 PFU/cell and incubated in a $CO_2$-incubator at 30° C., 34.5° C., and 39.1° C. Virus harvsts were prepared at 4 hr after infection at 34.5° C. to determine the amount of infectious virus present immediately after the absorption and penetration of the input virus, and after 10 days, 4 days and 3 days of incubation, respectively, at 30° C., 34.5° C., and 39.1° C. Virus harvests were plaque titrated at 34.5° C. and at 39.1° C. in RAB-9 cells as described in U.S. Pat. No. 4,514,497. The results are shown in Table 4 below.

TABLE 4

Replication of IBRV(NG) dl TK clone 1

| Temperature of Virus Growth | Time Postinfection Harvested | Virus Yield (PFU/ml) when plaque titrated at: 34.5° C. | 39.1° C. |
|---|---|---|---|
| 34.5° C. | 4 hr | $1.8 \times 10^2$ | $1.4 \times 10^2$ |
| 34.5° C. | 4 days | $2.3 \times 10^7$ | $2.1 \times 10^7$ |
| 30° C. | 10 days | $1.1 \times 10^6$ | $1\ 3 \times 10^6$ |
| 39.1° C. | 3 days | $6.0 \times 10^6$ | $8.0 \times 10^6$ |

Table 4 demonstrates that after 4 days of incubation at 34.5° C., IBRV(NG) dl TK clone 1 multiplied from about $10^2$ PFU/ml to about $2\times10^7$ PFU/ml and that this titer was attained regardless of whether the plaque titration was performed at 34.5° C. or 39.1° C. This clearly indicates that the virus is temperature resistant. Table 4 also demonstrates that titers of about $10^6$ and $10^7$ PFU/ml, respectively, were obtained when harvests were made at 10 and 3 days, respectively, at 30° C. or 39.1° C. Again, the same titers were formed regardless of whether the plaque titration was at 34.5° C. or 39.1° C. Thus, it is clear that this virus can grow to high titers over a broad range of temperatures, specifically, from 30° C. to 39.1° C. or higher.

While this invention has been described in detail with reference to specific embodiments thereof, it will be apparent to one skilled in the art that various changes and modifications can be made therein without departing from the spirit and scope thereof.

We claim:

1. An infectious bovine rhinotracheitis virus which fails to produce any functional TK as a result of a deletion in the tk gene.

2. The infectious bovine rhinotracheitis virus as claimed in claim 1, wherein said deletion is about 10 to 1500 bp in size.

3. The infectious bovine rhinotracheitis virus as claimed in claim 2, wherein said deletion is about 75 to 750 bp in size.

4. The infectious bovine rhinotracheitis virus as claimed in claim 1, wherein said virus is temperature resistant.

5. The infectious bovine rhinotracheitis virus as claimed in claim 1, wherein an oligonucleotide linker is present in the deletion site of the tk gene.

6. The infectious bovine rhinotracheitis virus as claimed in claim 5, wherein said linker is about 7 to 50 nucleotides in length.

7. The infectious bovine rhinotracheitis virus as claimed in claim 1, wherein said virus has the identifying characteristics of IBRV(NG) dl TK clone 1 (ATCC No. VR-2112).

8. The infectious bovine rhinotracheitis virus as claimed in claim 1, wherein said virus is lyophilized.

9. An infectious bovine rhinotracheitis virus which fails to produce any functional TK as a result of a deletion in the tk gene produced by the process comprising:

(1) constructing a hybrid plasmid comprising a cloning vector and a DNA fragment of IBRV containing substantially all of the IBRV tk gene;

(2) co-transfecting, in tk+ host cells, the hybrid plasmid of step (1) with infectious DNA from a tk− IBRV mutagen-induced mutant;

(3) selecting, in tk− host cells, for tk+ IBRB from the virus produced in step (2);

(4) deleting DNA sequences from the hybrid plasmid of step (1) such that less than substantially all of the IBRV tk gene is present;

(5) co-transfecting, in tk+ host cells, IBRV tk+ DNA derived from the tk+ IBRV obtained in step (3) with the resulting tk− hybrid plasmid of step (4); and (6) selecting, in tk− host cells, for tk− IBRV from the virus produced in step (5) so as to produce tk− IBRV mutants which fail to produce any functional TK as a result of a deletion in the tk gene.

10. The infectious bovine rhinotracheitis virus as claimed in claim 9, wherein said deletion is about 10 to 1500 bp in size.

11. The infectious bovine rhinotracheitis virus as claimed in claim 10, wherein said deletion is about 75 to 750 bp in size.

12. The infectious bovine rhinotracheitis virus as claimed in claim 9, wherein the tk− IBRV mutagen-induced mutant in step (2) is a temperature-resistant mutant such that the resulting mutant in step (6) is both temperature resistant and a tk− deletion mutant.

13. The infectious bovine rhinotracheitis virus as claimed in claim 9, additionally comprising step (7):

(7) propagating the resulting IBRV which fails to produce any functional TK as a result of a deletion in the tk gene of step (6) at a non-permissive temperature for a temperature-sensitive virus so as to select for and produce a temperature-resistant IBRV which fails to produce any functional TK as a result of a deletion in the tk gene.

14. The infectious bovine rhinotracheitis virus as claimed in claim 9, wherein an oligonucleotide linker is present in the deletion site of the IBRV DNA of step (4) while retaining IBRV DNA sequences adjacent to each side of the deletion site.

15. The infectious bovine rhinotracheitis virus as claimed in claim 14, wherein said linker is about 7 to 50 nucleotides in length.

16. The infectious bovine rhinotracheitis virus as claimed in claim 9, wherein said virus is lyophilized.

17. The infectious bovine rhinotracheitis virus as claimed in claim 9, wherein said cloning vector is selected from the group consisting of pBR322, pMB9, pBR325, pKH47, pBR328, pHC79, phage Charon 28, pKB11, pKSV-10, pMAR420 and oligo (dG)-tailed pBR322.

18. The infectious bovine rhinotracheitis virus as claimed in claim 17, wherein said cloning vector is pBR322.

19. The infectious bovine rhinotracheitis virus as claimed in claim 9, wherein said hybrid plasmid of step (1) is pLATK dl NdeI.

20. The infectious bovine rhinotracheitis virus as claimed in claim 9, wherein in step (4) the IBRV DNA sequences adjacent to each side of the deletion are at least 400 bp in size.

21. The infectious bovine rhinotracheitis virus as claimed in claim 9, wherein the resulting hybrid plasmid of step (4) is pLATK dl NdeI dl BglI/NG/SstI.

22. The infectious bovine rhinotracheitis virus as claimed in claim 9, wherein said tk+ host cells are selected from the group consisting of RAB-9 (ATCC No. CRL-1414); primary rabbit kidney cells, secondary rabbit kidney cells; rabbit cornea (SIRC) cells (ATCC No. CCL-60), rabbit kidney (LLC-RK1) cells (ATCC No. CCL-106), embryo bovine trachea (EBTR) cells (ATCC No. CCL-44), bovine turbinate (BT) cells (ATCC No. CRL-1390), and bovine kidney (MDBK) cells (ATCC No. CCL-22).

23. The infectious bovine rhinotracheitis virus as claimed in claim 22, wherein said tk+ host cells are RAB-9.

24. The infectious bovine rhinotracheitis virus as claimed in claim 9, wherein the tk− IBRV mutagen-induced mutant is selected from the group consisting of the non-temperature-resistant bromovinyldeoxyuridine-resistant IBRV mutant of IBRV(P8-2) and the temperature-resistant IBRV(B8-D53) (ATCC No. VR-2066).

25. The infectious bovine rhinotracheitis virus as claimed in claim 24, wherein the tk− IBRV mutagen-induced mutant is the temperature-resistant IBRV(B8-D53) (ATCC No. VR-2066).

* * * * *

UNITED STATES PATENT AND TRADEMARK OFFICE

CERTIFICATE OF CORRECTION

PATENT NO. : 4.703.011

DATED : October 27, 1987

INVENTOR(S) : Malon Kit, et. al.

It is certified that error appears in the above-indentified patent and that said Letters Patent is hereby corrected as shown below:

Column 1, line 4, between the Title and Field of Invention, insert -- The invention described herein was developed during the tenture of a Research Career Award to Saul Kit from the United States Public Health Service of Department of Health and Human Services. The Government has certain rights.--

Signed and Sealed this

Eighteenth Day of April, 1995

Attest:

BRUCE LEHMAN

*Attesting Officer*

*Commissioner of Patents and Trademarks*